United States Patent
Gjerde et al.

(10) Patent No.: US 6,579,459 B2
(45) Date of Patent: *Jun. 17, 2003

(54) SYSTEM AND METHOD FOR PERFORMING POLYNUCLEOTIDE SEPARATIONS USING LIQUID CHROMATOGRAPHY

(75) Inventors: Douglas T. Gjerde, Saratoga, CA (US); Robert M. Haefele, Campbell, CA (US); David W. Togami, San Jose, CA (US)

(73) Assignee: Transgenomic, Inc., Omaha, NE (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/086,301

(22) Filed: Feb. 28, 2002

(65) Prior Publication Data

US 2002/0185441 A1 Dec. 12, 2002

Related U.S. Application Data

(63) Continuation of application No. 09/828,346, filed on Apr. 5, 2001, now Pat. No. 6,491,821, which is a continuation of application No. 09/350,774, filed on Jul. 9, 1999, now Pat. No. 6,251,272, which is a continuation of application No. 09/081,040, filed on May 18, 1998, now Pat. No. 5,997,742, which is a continuation-in-part of application No. 08/748,376, filed on Nov. 13, 1996, now Pat. No. 5,772,889.

(51) Int. Cl.[7] ............................................. B01D 15/08
(52) U.S. Cl. ..................... 210/635; 210/656; 210/198.2; 435/6; 536/25.4
(58) Field of Search ................................. 210/635, 656, 210/659, 198.2; 436/6; 536/23.1, 25.4

(56) References Cited

U.S. PATENT DOCUMENTS

| | | | | |
|---|---|---|---|---|
| 5,772,889 A | * | 6/1998 | Gjerde | 210/635 |
| 5,972,222 A | * | 10/1999 | Gjerde | 210/635 |
| 5,997,742 A | * | 12/1999 | Gjerde | 210/635 |
| 6,017,457 A | * | 1/2000 | Gjerde | 210/635 |
| 6,024,878 A | * | 2/2000 | Gjerde | 210/635 |
| 6,030,527 A | * | 2/2000 | Gjerde | 210/198.2 |
| 6,136,195 A | * | 10/2000 | Taylor | 210/635 |
| 6,156,206 A | * | 12/2000 | Gjerde | 210/635 |
| 6,174,441 B1 | * | 1/2001 | Gjerde | 210/635 |
| 6,342,161 B1 | * | 1/2002 | Gjerde | 210/635 |

* cited by examiner

Primary Examiner—Ernest G. Therkorn
(74) Attorney, Agent, or Firm—Keith A. Johnson

(57) ABSTRACT

Improved liquid chromatography systems having components made of titanium, stainless steel, or organic polymeric material are useful in the separation of polynucleotide fragments, particularly large fragments of double-stranded polynucleotides, by Matched Ion Polynucleotide Chromatography (MIPC). The titanium, stainless steel, or polymeric components are treated so that they do not release multivalent cations into aqueous solutions flowing through the chromatography system. Alternatively, or in addition to utilizing materials made of the components listed above, a multivalent cation capture resin placed upstream of the separation column can be employed to remove multivalent ions from the system. The multivalent cation capture resin can be contained in a guard disk, a guard column, or a guard cartridge. Novel methods for separating mixtures of polynucleotide fragments into fractions based on their molecular weight by Matched Ion Polynucleotide Chromatography and slalom chromatography utilize the liquid chromatographic systems described above.

55 Claims, 9 Drawing Sheets

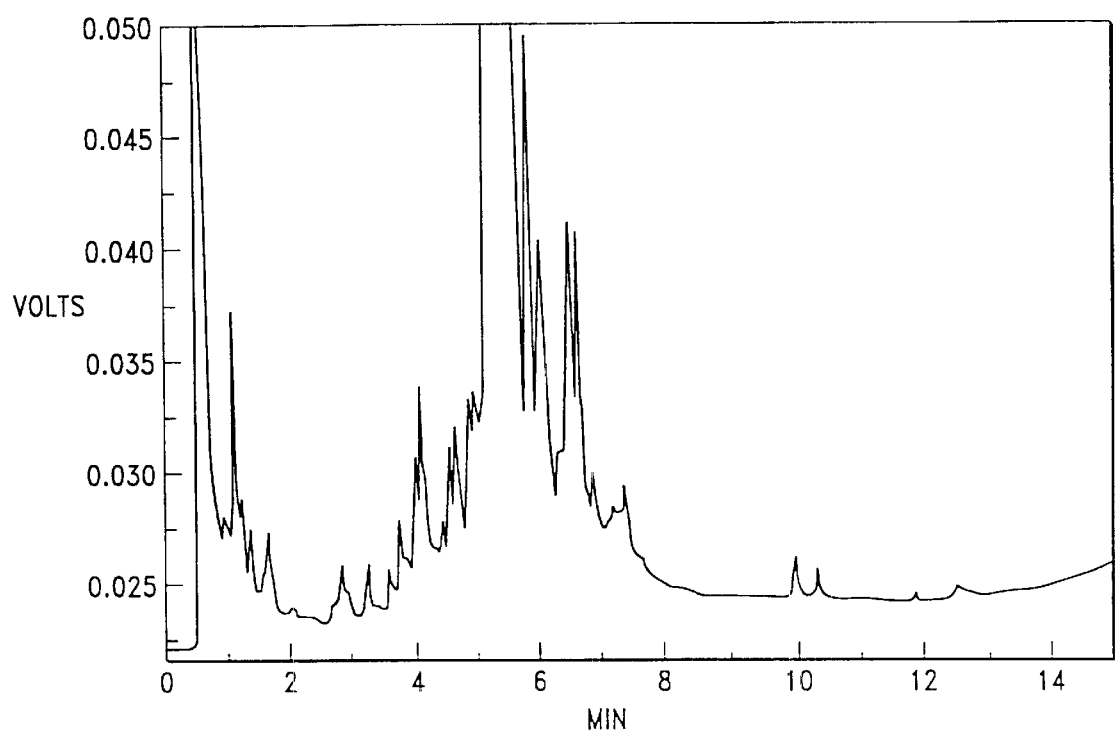
FIG.—15
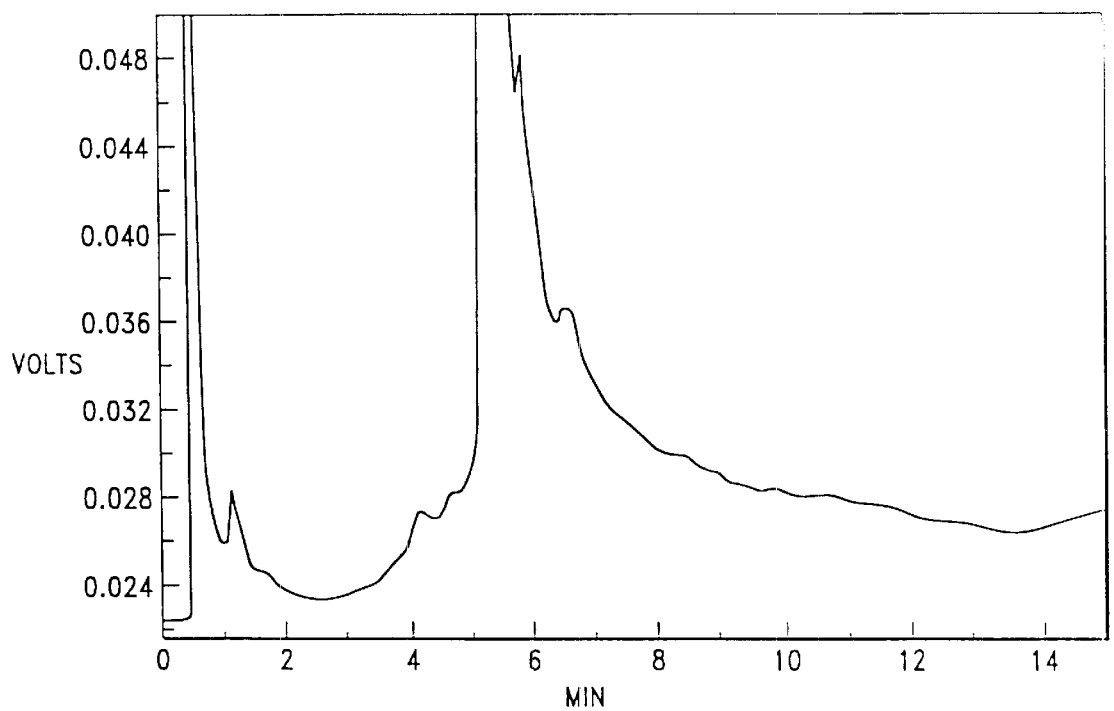
FIG.—16

SYSTEM AND METHOD FOR PERFORMING POLYNUCLEOTIDE SEPARATIONS USING LIQUID CHROMATOGRAPHY

RELATIONSHIP TO COPENDING APPLICATIONS

This is a continuation of U.S. patent application Ser. No. 09/828,346 filed Apr. 5, 2001, now U.S. Pat. No. 6,491,821 which is a continuation of U.S. patent application Ser. No. 09/350,774 filed Jul. 9, 1999 (now U.S. Pat. No. 6,251,272), which is a continuation of U.S. patent application Ser. No. 09/081,040 filed May 18, 1998 (now U.S. Pat. No. 5,997, 742), which is a continuation-in-part of U.S. patent application Ser. No. 08/748,376 filed Nov. 13, 1996 (now U.S. Pat. No. 5,772,889).

FIELD OF THE INVENTION

The present invention is directed to the separation of polynucleotide fragments by liquid chromatography. More specifically, the invention is directed to a liquid chromatography system and method, such as Matched Ion Polynucleotide Chromatography or slalom chromatography, which enhances the separation of polynucleotides.

BACKGROUND OF THE INVENTION

Separation of polynucleotides is a focus of scientific interest, and numerous researchers have been attempting to achieve technical improvements in various aspects of polynucleotide separation. Anion exchange separation and reverse phase ion pair chromatography are among the most frequently used methods for separating polynucleotides.

Previous work has focused on developing rapid, high resolution separations, developing separations based on the size of the polynucleotide fragment rather than the base sequence of the fragment, and on developing the ability to collect fractions of polynucleotides.

W. Bloch (European patent publication No. EP 0 507 591 A2) demonstrated that, to a certain extent, length-relevant separation of polynucleotide fragments was possible on nonporous anion exchangers with tetramethylammonium chloride (TMAC) containing mobile phases. Y. Ohimya et al. (*Anal. Biochem.*, 189:126–130 (1990)) disclosed a method for separating polynucleotide fragments on anion exchange material carrying trimethylammonium groups. Anion exchangers with diethylaminoethyl groups were used by Y. Kato et al. to separate polynucleotide fragments (*J. Chromatogr.*, 478:264 (1989)).

An important disadvantage of anion exchange separations of double-stranded polynucleotides is the differing retention behavior of GC- and AT-base pairs. This effect makes separation according to molecular size impossible. Another important drawback of the anion exchange methodology is the necessity to use salts and buffers for elution, thus making subsequent investigation of the polynucleotide molecule fractions very difficult.

U.S. Pat. No. 5,585,236 (1996) to Bonn et al. describes a method for separating polynucleotides using what was characterized as reverse phase ion pair chromatography (RPIPC) utilizing columns filled with nonporous polymeric beads. High resolution, rapid separations were achieved using an ion-pairing reagent, triethylammonium acetate, and acetonitrile/water reagent mobile phase gradient. This work is important because it is the first separation to give size-dependent, sequence-independent separation of double-stranded polynucleotides by chromatography. These separations are comparable to gel electrophoresis-compatible separations, currently the most widely used technology for polynucleotide separations. Bonn's work makes it possible to automate separations based on the size or on the polarity of polynucleotides.

In the course of our work on separation of polynucleotides using the method developed by Bonn et al., with HPLC instrumentation and columns as described by Bonn, we discovered a degradation effect on the separation of double-stranded polynucleotides after long-term column usage (i.e., greater than about 50 injections). This degradation effect has been generally observed as a loss of resolution for base pairs greater than 200, as illustrated in the chromatogram of FIG. 1. As the degradation worsens, increasingly short fragments of polynucleotides are affected, as shown in FIG. 2. Eventually, the polynucleotides do not elute from the system. As such, the degradation effect or decreasing resolution appears to be a function of the length of the polynucleotide fragment being separated.

There is no published chemical mechanism which would explain such a degradation effect that distinguishes between different size fragments while using reverse phase chromatography. Therefore, we first examined our procedure for packing the column. We realized that the molecules that we were attempting to separate were several magnitudes larger in size than those conventionally separated by reverse phase ion pair liquid chromatography. We suspected that hydrodynamic flow through the column was adequate for short polynucleotide fragments, but was being disrupted for larger fragments. In other words, perhaps the longest fragments were being partially sheared. However, we were unable to identify a packing procedure that would discriminate between short and long fragments of polynucleotides.

Although we could not conceive a mechanism by which chemical contamination could produce these unusual results, we nevertheless examined contamination of one or more of the various "pure" reagents employed in liquid chromatography. After testing each of the reagents for contamination, we determined that this was not the source of the problem. This is not surprising, since the mobile phases used are not corrosive.

Subsequent clean-up of the column with injections of tetrasodium ethylenediaminetetraacetic acid (EDTA), a metal-chelating agent, largely restored chromatographic resolution, as shown in FIG. 3. Putting a chelating additive into the mobile phase can provide some protection to the column. Without wishing to be bound by theory, there are several mechanisms by which a chelating reagent can provide protection or restore the instrument or column. One mechanism is the chelating reagent binds the free metal ions in solution, thus preventing any interaction of the metal ions with the DNA. Another mechanism is the chelating reagent coats colloidal metal ions, thereby preventing interaction of the colloidal metal ions with the DNA. The colloidal metal can be introduced from the mobile phase, injected into the mobile phase, or can be released from wetted surfaces in the fluid path. If the chelating reagent is water soluble, it can eventually dissolve the colloidal metals.

We were successful in adding small amounts (i.e., 0.1 mM) of tetrasodium EDTA to the mobile phase without significant changes to the chromatography. However, this concentration of EDTA was not sufficient to protect the columns in all of the stainless steel HPLC instruments and columns that were tested. There can be cases where the amount of metal ions present or generated are at a concentration where adding a chelating reagent will coat or bind the metal ions. In these cases, addition of a small amount of chelating reagent can allow the successful separation of DNA fragments.

We tested the use of larger amounts of chelator additive in the mobile phase and found that addition of 10 mM of tetrasodium EDTA impaired the separation of polynucleotides. It was still uncertain that this higher concentration of chelating agent provided an acceptable protective benefit. While use of EDTA injected into the mobile phase (via the HPLC sample injection valve) demonstrated that the column can be regenerated, addition of chelating agents to the mobile phase is not an ideal solution to the problem as it can hamper subsequent use or analysis of the polynucleotide fragments.

We then discovered that placing a cation exchange resin in the flow path of the mobile phase removed the problem. Guard disks were prepared containing a gel-type iminodiacetate resin with an ion exchange capacity of 2.5 mequiv/g (tested with Cu(II)). FIG. 4 shows a chromatogram obtained when the guard disk was positioned directly in front of the sample injection valve. FIG. 5 shows a chromatogram obtained when the guard disk was placed directly in front of the separation column (i.e., between the injection valve and the column). Attempts to separate polynucleotides on the stainless steel HPLC system without the use of guard disks or guard columns containing cation exchange resin or chelating resin resulted in rapid deterioration of the chromatographic separation.

From the improved results obtained by placing a cation exchange resin in the flow path of the mobile phase, we concluded that whatever was causing the peak distortion, probably ionic contaminants, was capable of binding to the cation exchange resin. Whatever was causing the fragment size-dependent distortion of the peaks had been removed by the cation exchange resin.

Ionic contamination of the system can logically originate in one or more of several sources. The most significant sources of metal ions are HPLC components containing fritted filters made of stainless steel. Fritted filter components are used in mobile phase filters, check valve filters, helium spargers, mobile phase mixers, in-line filters, column frits, and other parts of the HPLC. Frits are commonly located at each end of a separation column in order to contain the particulate packing material within the column. The frit at the head of a column also serves to trap particulate material. Trapped particulate materials can be metal ions released from another part of the liquid chromatography system. The large surface area associated with any particular fritted component can contribute to faster solubilization of metals and release of ions. Thus, the ionic contamination from a fritted component can arise in at least two ways. First, the component can be a source of ionic material. Second, it can be a means for trapping ionic material.

Ionic contamination from metals can exist in two forms. One form is dissolved metal ions. In another form, metals ions can exist in the colloidal state. For example, colloidal iron can be present, even in "high purity" 18 megohm water. Any metal or other ion that can interact with polynucleotides in the manner described could cause potentially harmful chromatographic effects when the metal becomes trapped on the chromatographic column. Magnesium and/or calcium and other ions can be present in samples such as PCR products. However, at the concentrations typically used, magnesium ions present in PCR products do not harm the peak separation.

Metal ion contamination such as colloidal iron can be released from frits, travel to other parts of the HPLC and then be trapped. These types of contaminants will interfere with DNA in solution or after having been released and trapped on a critical component of the HPLC such as the column, an inline filter in front of the detector, or at a back pressure device located after the detector.

In order to test our hypothesis that soluble metals and, potentially, other ions were causing loss of peak resolution during polynucleotide separations, we challenged the HPLC system with iron, chromium, and nickel. Known concentrations of these three metal ions were added to a polynucleotide standard (pUC18 DNA-Hae III digest). The polynucleotide/metal ion solutions were then injected into the HPLC.

Chromium (III) ions (prepared from $CrK(SO_4)_2$ did not degrade the separation when present in the sample at 9 mM. However, the sample contained 100 mM EDTA as a preservative against enzymatic degradation during storage, and much of the chromium could have been bound in an EDTA complex. However, when chromium was present at 90 mM, fragment size-dependent degradation of peaks occurred. At 900 mM chromium, no peaks could be detected. Several hours later, a sample containing 50 mM Cr(III) showed complete loss of the separation peaks.

The same protocol using Ni(II) (prepared from $Ni_2SO_4$) showed substantially no effect on peak shape, although some peak broadening was observed at 0.1 M Ni(II).

With Fe(III) (prepared from $FeNH_4(SO_4)_2$), the effect was less than with Cr(II). An injection of 900 $\mu$M of Fe(III) in the polynucleotide standard showed no effect. However, an injection of 2700 $\mu$M resulted in a loss of all peaks. There was some indication that the results were time-dependent, with the full effect becoming apparent several minutes after preparation of the metal/polynucleotide sample.

The contact times and metal concentrations of the experiments described above were several orders of magnitude higher than would be found in a stainless steel HPLC system used for polynucleotide separations. Also, none of the experiments indicated how any reaction could be dependent on the size of the polynucleotide fragment. However, these data show the relative effect on separations of some of the metals found in stainless steel on polynucleotide separation.

As an example of the effects of stainless steel, placement of a previously used stainless steel frit as an inline frit in front of the column resulted in no peaks being eluted from the column, even after short exposure of the frit to the fluid path. In this case all of the DNA was lost in the separation. This means that either DNA was taken up by the frit, or the frit released material that either disrupted the separation of DNA on the column or within the fluid path to the column and detector.

The effect of metals on the reverse phase column separation of polynucleotides or an effect that discriminated according to fragment size has not been reported in the literature. There are, in fact, only a limited number of publications on the chromatographic separation of polynucleotides; most of which focus on single-stranded polynucleotides. Separation of single-stranded polynucleotides has been performed routinely by many workers, but this is usually on very short lengths of polynucleotide fragments (usually less than 100-mer, with 25-mer the average length), where, based on our observations of double-stranded polynucleotides, we would expect the degradation effect to be much less pronounced.

Gunther Bonn and his colleagues have developed the world's leading chromatographic method for separating double-stranded polynucleotides. Bonn's work was performed on a stainless steel HPLC system with stainless steel hardware, including stainless steel frits. Based on our discovery, we concluded that the effect of metal contamination on polynucleotide separations was never reported by Bonn or others because the amount of dissolved and particulate metals in their stainless steel systems was below the threshold where degradation of the separation occurs and the systems worked adequately to produce good peak separations. Also, our work was carried out over a longer period, perhaps giving sufficient time for accumulation of contaminants within the system.

Metal-free or titanium instrumentation is commonly used in protein separations, for reasons peculiar to the art of protein separation. For example, the activity of a protein can be affected if a metal is present. If the protein is intended to be collected and studied, separation is generally performed in a metal-free environment. Also, protein separations use particular mobile phases that can be corrosive to stainless steel HPLC equipment.

Although metal-free or titanium systems are generally used in the separation of proteins for the reasons discussed above, it has been demonstrated that the use of metal-free or titanium systems is not necessary to maintain the integrity of the separation and that stainless steel HPLC systems show equivalent performance (Herold, M. et al., *BioChromatography*, 10:656–662 (1991)). In fact, Hewlett-Packard, one of the leading manufacturers of HPLC systems, now recommends stainless steel systems for use in protein separations.

Because of the success of using stainless steel components in protein separations, and because the use of stainless steel systems for polynucleotide separations had been shown to be successful in the past, there had previously been no indication of the requirement to use non-metal or titanium system components for liquid chromatographic separation of polynucleotide fragments.

Our subsequent experiments showed that even if titanium or PEEK fluid path components are used, then some treatment was necessary before the components could be used for Matched Ion Polynucleotide Chromatography. Although an improvement, our initial use of titanium frits did not give consistent results. Treatment of the frits with dilute nitric acid and then with a chelating agent did improve the performance of the instrument. Similarly, as shown in the examples, PEEK frits were not consistently suitable for MIPC, but acid treatment did improve their performance.

Finally, degassing the fluid before it enters the liquid chromatography system removes the oxygen. This process will inhibit the oxidation and production of metal ions in stainless steel or titanium or other tubing containing iron. The use of a degasser to remove oxygen can help the MIPC separation. This is probably because the need for an ion contaminant free fluid path is much more critical in MIPC than in prior art separation processes. The use of the precautions of the method and system of the present invention has been found to be much more critical for double stranded DNA than for single stranded DNA separations.

As Bonn and coworkers demonstrated, stainless steel can be an excellent material to be used for the fluid path of DNA separations. However, it is difficult to keep the stainless steel surface free of contaminants which interfere with MIPC, especially as the surfaces age.

SUMMARY OF THE INVENTION

It is an object of the present invention to achieve optimum peak separations during the separation of polynucleotides (e.g. double-stranded polynucleotides such as dsDNA) using Matched Ion Polynucleotide Chromatography or slalom chromatography.

It is another object of the invention to extend the maximum useful life of a chromatographic separation column by protecting the column from the potentially deleterious effects of ionic contaminants present within the liquid chromatography system.

The invention is a system and method for separating polynucleotide fragments whereby the effects of metal or other ionic contamination are avoided. Although the exact mechanism of the degradation effect remains unknown, we have determined that, by avoiding stainless steel or other metal components that can react with phosphate and/or nitrogen groups or unknown groups of the polynucleotides, we are able to separate polynucleotide fragments to high resolution. This is accomplished by any combination of several measures: use of non-metal or titanium frits in the column; use of non-metal or titanium frits in the HPLC system; use of an ion-binding material upstream of the sample injection valve and/or separation column; use of non-metal or titanium system components (e.g., pump heads, tubing, pulse dampeners) anywhere within the system that mobile phase comes in contact with a surface; use of a pre-treatment, non-limiting examples of which include an acid wash treatment, a coating treatment, or treatment with a chelating reagent of any component surface anywhere within the system that comes into contact with mobile phase in order to eliminate multivalent cation contamination arising from the surface; use of a mobile phase additive that can capture or bind metals or other ions; use of a degassing system for removing oxygen from the mobile phase for preventing oxidation of metals in the fluid path.

In one aspect, the present invention discloses an improved liquid chromatography system for separating a mixture of polynucleotide fragments. The separation can be based on the size or the polarity of the fragments. The fragments can be double stranded. The fragments comprise at least 5 base pairs. The polynucleotide fragments can be covalently coupled to a detectable tag such as radioisotopes and fluorescent dyes. In a preferred embodiment, the system comprises a chromatographic column containing a separation bed of Matched Ion Polynucleotide Chromatography (MIPC) separation particles held in the column between porous frits positioned at each end of the column. The column has an inlet, an injection valve which is in communication with the inlet by means of a flow path, and mobile phase supply means which is (are) in communication with the injection valve by means of at least one flow path. Multivalent cation capture resin capable of removing multivalent cations from aqueous solutions is positioned in the flow path. Using the system of the invention, any multivalent cation contaminants in the flow path are removed before they contact the separation bed.

The multivalent cation capture resin can be cation exchange resin or chelating resin, but is preferably cation exchange resin having an ion exchange moiety selected from the group consisting of iminodiacetate, nitriloacetate, acetylacetone, arsenazo, hydroxypyridinone, and 8-hydroxyquinoline groups. Cation exchange resin having an iminodiacetate group is particularly preferred. The multivalent cation capture resin is preferably contained in a guard disk, guard column, or guard, and is preferably positioned in the flow path between the mobile phase supply means and the injection valve. The system further can also include multivalent cation capture resin (preferably contained in a guard disk) positioned in the flow path between the injection valve and the separation column.

The components of the system have process solution-contacting surfaces which contact process solutions held within the components or flowing through the components. The process solution-contacting surfaces are preferably material which does not contain or release multivalent cations. The material is most preferably titanium, coated stainless steel, or organic polymer. The surfaces are preferably subjected to a multivalent cation removal treatment so that they do not release multivalent cations. The treatment can include contacting the surfaces with aqueous solution containing nitric acid, phosphoric acid, pyrophosphoric acid, or chelating agents. In one embodiment, the process solutions include a mobile phase additive (e.g. EDTA) that can capture or bind multivalent cation contaminants. The process solutions preferably are exposed to a degassing system for removing oxygen.

In another aspect, the system comprises a chromatographic column containing a separation bed of MIPC separation particles held in the column between porous frits positioned at each end of the column. The column has an inlet, an injection valve which is in communication with the inlet by means of a conduit, and mobile phase supply means which is (are) in communication with the injection valve by means of at least one conduit. The frits have process solution-contacting surfaces which are made of material which does not release multivalent cations into aqueous solutions flowing through the frits or collect material from other sources. The material is most preferably titanium, coated stainless steel, or organic polymer. The surfaces preferably are subjected to a multivalent cation removal treatment. The treatment can include treatment with nitric acid, phosphoric acid, pyrophosphoric acid, or chelating agents. In one embodiment, the process solutions include a mobile phase additive (e.g. EDTA) that can capture or bind multivalent cation contaminants. The process solutions preferably are exposed to a degassing system for removing oxygen.

The process solution-contacting surfaces of other system components (such as the chromatographic column, injection valve, mobile phase supply means, and conduits) are also preferably material which does not contain or release multivalent cations. The system also preferably includes multivalent cation capture resin positioned between the mobile phase supply means and the injection valve. The multivalent capture resin is preferably cation exchange resin or chelating resin, which is preferably contained in a guard column or guard cartridge. The system can also include multivalent cation capture resin, preferably contained in a guard disk, positioned between the injection valve and the separation column.

Also disclosed herein are methods for improving the separation of polynucleotide fragments into fractions during MIPC using a liquid chromatographic column containing a separation bed comprising MIPC separation particles. The separation can be based on the size or polarity of the fragments. One method comprises supplying and feeding solutions entering the liquid chromatographic separation column with components having process solution-contacting surfaces which are made of material which does not release multivalent cations into aqueous solutions held therein or flowing through the column. The process solution-contacting surfaces of the components are preferably titanium, coated stainless steel, or organic polymer. The surfaces are preferably subjected to a multivalent cation removal treatment. The treatment can include contacting the surface with an aqueous solution containing nitric acid, phosphoric acid, pyrophosphoric acid, or chelating agents. In one embodiment, the process solutions include a mobile phase additive (e.g. EDTA) that can capture or bind multivalent cation contaminants. The process solutions preferably are exposed to a degassing system for removing oxygen. The MIPC separation particles are preferably alkylated nonporous polymer beads having an average diameter of about 1–100 microns.

The method can further include contacting mobile phase solutions and sample solutions entering the column with multivalent cation capture resin before the solutions enter the column to protect the separation bed from multivalent cation contamination. The method is used to separate single and double stranded DNA, and preferably used for separating double-stranded polynucleotide fragments, particularly those having 5 or more base pairs.

In an alternative method for improving the separation of polynucleotide fragments into fractions during MIPC using a liquid chromatographic column containing a separation bed comprising MIPC separation particles, process solutions are contacted with multivalent cation capture resin before the solutions enter the chromatographic column in order to protect the separation bed from multivalent cation contamination. The separation can be based on the fragment size or polarity. The multivalent cation capture resin can be cation exchange resin or chelating resin, but is preferably a cation exchange resin having an ion exchange moiety selected from the group consisting of iminodiacetate, nitriloacetate, acetylacetone, arsenazo, hydroxypyridinone, and 8-hydroxyquinoline groups. Cation exchange resin having an iminodiacetate group is particularly preferred. The multivalent cation capture resin is preferably contained in a guard disk, guard column, or guard cartridge. The MIPC separation particles are preferably nonporous beads having an average diameter of about 1–100 microns. The particles have been subjected to an acid wash treatment during manufacture in order to eliminate multivalent cation contaminants. The method can further include supplying and feeding solutions entering the column with components having process solution-contacting surfaces which are material which does not release multivalent cations into process solutions so that the contents of the column are protected from multivalent cation contamination. The process solution-contacting surfaces of the components are preferably titanium, coated stainless steel, and organic polymer. The surfaces are subjected to a multivalent cation removal treatment. The treatment can include contacting the surfaces with an aqueous solution containing nitric acid, phosphoric acid, pyrophosphoric acid, or chelating agents. In one embodiment, the process solutions include a mobile phase additive (e.g. EDTA or crown ether) that can capture or bind multivalent cation contaminants. The process solutions preferably are exposed to a degassing system for removing oxygen. The method is preferably used for separating double-stranded polynucleotide fragments, particularly those having 10 or more base pairs.

Also disclosed herein is a method for improving separation of polynucleotide fragments during slalom chromatography using a liquid chromatographic column containing a separation bed comprising slalom chromatography DNA separation particles. The method comprises contacting the process solutions with multivalent cation capture resin before the solutions enter the chromatographic column in order to protect the separation bed from multivalent cation contamination. The multivalent cation capture resin can be cation exchange resin or chelating resin, but is preferably cation exchange resin having an ion exchange moiety selected from the group consisting of iminodiacetate, nitriloacetate, acetylacetone, arsenazo, hydroxypyridinone, and 8-hydroxyquinoline groups. Cation exchange resin having an iminodiacetate group is particularly preferred. The multivalent cation capture resin is preferably contained in a guard disk, guard column, or guard cartridge.

The method can further include supplying and feeding solutions entering the column with components having process solution-contacting surfaces which are material which does not release multivalent cations into process solutions so that the contents of the column are protected from multivalent cation contamination. The process solution-contacting surfaces of the components are preferably titanium, coated stainless steel, or organic polymer. The surfaces are preferably subjected to a multivalent cation removal treatment. The treatment can include contacting the surfaces with an aqueous solution containing nitric acid, phosphoric acid, pyrophosphoric acid, or chelating agents. In one embodiment, the process solutions include a mobile phase additive (e.g. EDTA) that can capture or bind multivalent cation contaminants. The process solutions preferably are exposed to a degassing system for removing oxygen. The slalom chromatography method is preferably used for separating double-stranded polynucleotide fragments, particularly those having 5000 or more base pairs.

BRIEF DESCRIPTION OF THE DRAWINGS

FIG. 15 shows separation of a 20-mer oligonucleotide on a column having titanium frits.

FIG. 16 shows separation of the oligonucleotide as used in FIG. 15 but on a column having PEEK frits.

DETAILED DESCRIPTION OF THE INVENTION

Figure 1:
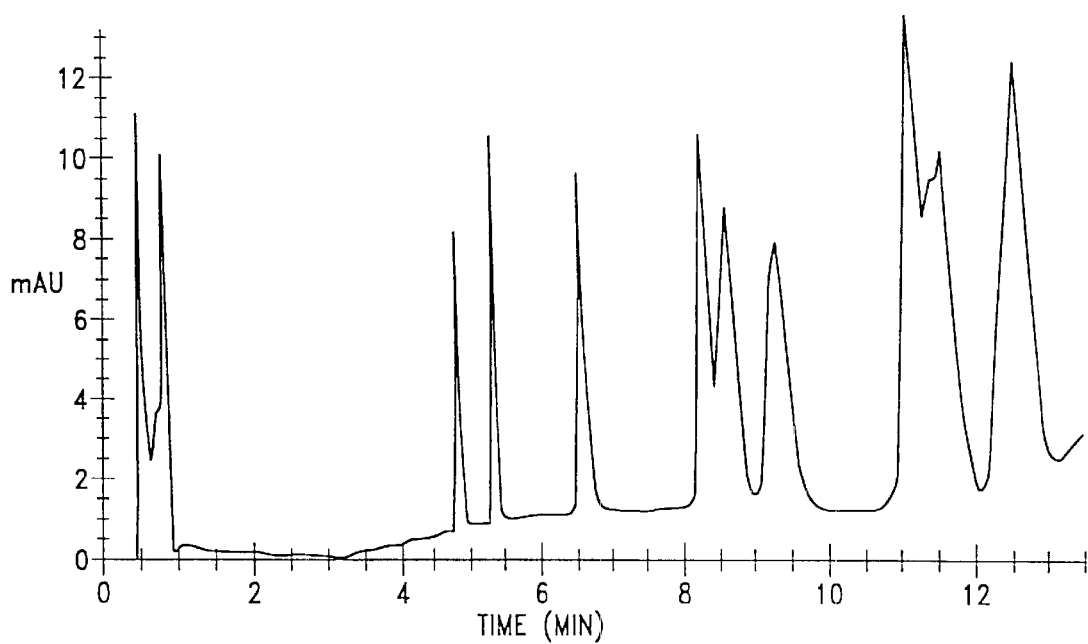
FIG. 1 shows a chromatogram of double-stranded DNA separation illustrating the degradation effect on peak separation caused by ionic contaminants present within the HPLC system. In this case, the degradation effect is greater than about 174 base pairs.

Matched Ion Polynucleotide Chromatography (MIPC) as used herein, is defined as a process for separating single and double stranded polynucleotides using non-polar beads which have a pore size which is effective to exclude the polynucleotides being separated, wherein the process uses counter ion agents, and uses an organic solvent to desorb the polynucleotide from the beads.

The term polynucleotide is defined as a linear polymer containing an indefinite number of nucleotides, linked from one ribose (or deoxyribose) to another via phosphoric residues. The present invention can be used in the separation of RNA or of double- or single-stranded DNA. For purposes of simplifying the description of the invention and not by way of limitation, the separation of double-stranded DNA will be described hereinafter, it being understood that all polynucleotides are intended to be included within the scope of this invention.

In parent application Ser. No. 08/748,376, filed Nov. 13, 1996, and in U.S. Pat. No. 5,585,236, the DNA separation process was characterized as reverse phase ion pair chromatography (RPIPC). However, since RPIPC does not incorporate certain essential characteristics described in the present invention, another term, MIPC, has been selected for this DNA separation process.

The system of the invention includes a chromatographic column containing a separation bed of MIPC separation particles held in the column between porous frits positioned at each end of the column. The term "MIPC separation particles" refers to any material which is capable of separating polynucleotide fragments by MIPC. The MIPC separation particles can be inorganic, including silica, zirconia, alumina, or other material; or can be polymeric, including crosslinked resins of polystyrene, polyacrylates, polyethylene, or other organic polymeric material. The only requirement for the MIPC separation particles is that they must have a surface that is either intrinsically hydrophobic or be bonded with a material that forms a surface having sufficient hydrophobicity to interact with a counter ion agent. Suitable MIPC separation particles are described in co-pending U.S. patent application Ser. Nos. 09/058,580 and 09/058,337 which are hereby incorporated by reference in their entirety.

As used herein, the term "nonporous" is defined to denote a bead which has surface pores having a diameter that is less than the size and shape of the smallest DNA fragment in the separation in the solvent medium used therein. Included in this definition are polymer beads having these specified maximum size restrictions in their natural state or which have been treated to reduce their pore size to meet the maximum effective pore size required.

The surface conformations of nonporous beads of the present invention can include depressions and shallow pit-like structures which do not interfere with the separation process. A pretreatment of a porous bead to render it nonporous can be effected with any material which will fill the pores in the bead structure and which does not significantly interfere with the MIPC process.

Pores are open structures through which mobile phase and other materials can enter the bead structure. Pores are often interconnected so that fluid entering one pore can exit from another pore. We believe that pores having dimensions that allow movement of the polynucleotides into the bead structure result in poorly resolved separations or separations that have very long retention times. In MIPC, however, the beads are "nonporous" and the polynucleotides do not enter the bead structure.

Suitable MIPC separation particles comprise alkylated nonporous polymer beads having an average diameter of about 1–100 microns, which are described in further detail in the "Methods" section below.

Figure 8:
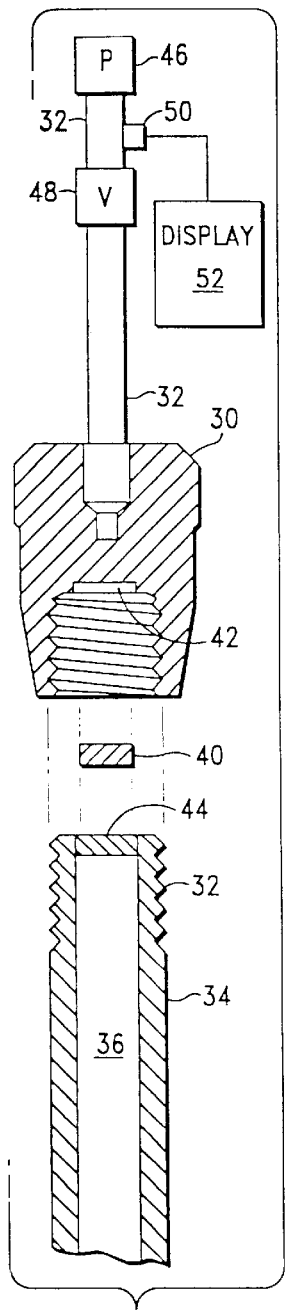
FIG. 8 shows placement of a chelating guard disk positioned between a chromatographic separation column and a column top, where the guard disk is in direct contact with a titanium frit at the top portion of the separation column.

Other components of the liquid chromatography system include an injection valve and one or more mobile phase supply means. Mobile phase supply means is (are) connected to the injection valve, and the injection valve is connected to the inlet of the chromatographic separation column, by means of conduit (e.g., tubing), as illustrated in FIG. 8.

The components of the liquid chromatography system have surfaces (i.e., "process solution-contacting surfaces") which contact process solutions held within the component (e.g., the mobile phase supply means) or flowing through the component (e.g., the porous frits, chromatographic column, injection valve, and conduits). The term "process solution" as used herein refers to any solution (such as a sample solution or mobile phase solution) which is contained within or flows through any component of the liquid chromatography system during liquid chromatography. The term "process solution-contacting surface" refers to any surface of a liquid chromatography system to which process solutions are exposed during performance of chromatographic separations.

The process solution-contacting surfaces of the porous frits on either end of the separation column must be made of material which does not release multivalent cations into aqueous solutions flowing through the column. The material is preferably titanium, coated stainless steel, or organic polymer, but is most preferably acid treated titanium as described hereinbelow. The term "coated stainless steel" as used herein refers to stainless steel that has been coated so that does not release, or is prevented from releasing, multivalent cations. A non-limiting example of a coating material is polytetrafluoroethylene (i.e., Teflon®). "Coated stainless steel" as used herein also refers to stainless steel that has been pre-treated with an agent such as EDTA or phosphoric acid which forms coordination complexes with multivalent metal ions.

"Passivated stainless steel" as used herein refers to stainless steel that has been treated with an agent that removes the oxidized metals and also metals that are easily oxidized such as iron. The most common passivating agent for stainless steel is nitric acid. Nitric acid will removed any oxidized metals, but will also remove iron that is located on the surface of the metal, leaving other metals such as chromium and nickel. Some chelating agents can coat and passivate. EDTA will first coat oxidized metals especially colloidal iron oxide particles. As treatment continues, the EDTA will bind and dissolve the iron oxide. However, as individual iron molecules leave the particle, other chelating molecules must coat the newly exposed surfaces for the surface to remain suitable for MIPC. A chelating agent does not passivate in the sense that it will only coat metal ions for which it is specific and will not dissolve non-oxidized metals. The chelating reagents used depend upon the type of ion contamination which is present. For example, Tiron chelating agent is selective for titanium and iron oxides. EDTA is selective for most metal oxides at pH 7. Other chelating reagents include cupferron, 8 hydroxyquinoline, oxine, and various iminodiacetic acid derivatives. If the chelating reagents are to be used as passivating reagents as well as coating reagents, then it is important the metal ion chelate complex, for example, EDTA-metal ion complex, is soluble in the fluid. Chelating reagents that form insoluble complexes, for example 8-hydroxyquinoline, perform coating functions only.

Without wishing to be bound by theory, it is believed that oxidized and positively charged metals, such as oxides of iron on the surface of stainless steel can trap negatively charged molecules such as DNA leading to degradation of the chromatographic separation, and that the pre-treatment masks or shields these surface charges. EDTA can be added, for example, in an amount sufficient to shield any surface sites which would interfere with the chromatographic separation. In one embodiment, a solution of a metal chelating agent such as EDTA can be applied in a batch process to coat the surface, for example by a single injection of EDTA solution into the HPLC system. In another embodiment, EDTA is included as an additive in the mobile phase.

Other components of the liquid chromatography system are preferably ketone (PEEK) or polyethylene. The preferred system tubing (i.e., conduit) is titanium, PEEK, or other polymeric material, with an inner diameter of 0.007". The preferred mobile phase inlet filters are composed of a porous, non-stainless steel material, which can be PEEK, polyethylene, or other polymeric material. The preferred solvent pump is also made of a non-stainless steel material; the pump heads, check valves, and solvent filters are preferably titanium, PEEK, or other polymeric material. The preferred degasser is an inline degasser placed prior to the pump inlet. The sample injection valve is also preferably titanium, PEEK, or other polymeric material. A standard detector and mobile phase reservoirs can be used, with no modifications necessary.

Materials such as titanium, PEEK and other organic polymers such as polyethylene, have been generally considered to be inert and preferred for the separation of biological molecules by processes in use before the development of MIPC. We have discovered that these materials, while inert for the prior art processes, can be a source of contaminants which interfere with the MIPC chromatographic separation. We have also observed that the interference with MIPC separation by these materials becomes more apparent during separations carried out at elevated temperatures, e.g. 57° C. as compared to 51° C.

In a preferred embodiment of the present invention, all of the process solution-contacting surfaces are subjected to a multivalent cation removal treatment to remove any potential source of multivalent cation contamination. These surfaces include the column inner surface, porous frits, conduits, mobile phase supply system, injector valves, mixers, pumpheads, and fittings. A non-limiting example of a multivalent cation removal treatment is an acid wash treatment. This wash treatment can include flushing or soaking and can include sonication. An example of an acid wash treatment is sonication of a PEEK or titanium frit in the presence of aqueous nitric acid solution, followed by sonication in water until a neutral pH is achieved. Other treatments include contacting the surfaces with chelating agents such as EDTA, pyrophosphoric acid, or phosphoric acid (e.g. 30% by weight phosphoric acid).

PEEK and titanium can be treated with dilute acids including nitric and hydrochloric acids. PEEK is not compatible with concentrated sulfuric or concentrated nitric acids. Titanium is not compatible with concentrated hot hydrochloric acid. Treatment with a chelating reagent can be performed before, but preferably after treatment with an acid. 20 mM tetrasodium EDTA is a preferred chelating reagent treatment.

The preferred treatment for titanium frits is sonication for 10 minutes with cold hydrochloric acid, sonication with water until neutral pH, 2 hour sonication with 0.5 M tetrasodium EDTA, storage several days in 0.5 M tetrasodium EDTA, sonication with water until neutral pH, and then washing with methanol, followed by drying. Preferred treatment for PEEK frits is sonication for 15–30 minutes each with THF, concentrated hydrochloric acid, 20% nitric acid, sonication with water until neutral pH, and then washing with methanol, followed by drying. Although this is a preferred treatment method, the effectiveness of this treatment of PEEK frits can depend on the vendor and lot of material treated. The success of the treatment also depends on the temperature of the DNA separation with higher column temperatures requiring the most complete removal of contamination. Although the mechanism is unknown, the effect of PEEK contamination is dependent on the sequence of the fragment (see Examples hereinbelow).

If the ionic contaminant is organic, then organic solvents or a combination of organic solvents and acids can be used. Also, organic ionic contaminants can require detergents, soaps or surfactants for removal from the surface. Nonionic contaminants such as greases and oils will also contaminate the separation column, generally leading to poor peak shape, but depending upon the size of the fragment. Nonionic organic contaminants such as oils will require detergents, soaps or surfactants to remove. Column tubing can be treated under sonication with Decalin (D5039, Sigma) to remove silicon greases and oils. Removal of colloidal metal oxides such as colloidal iron oxide can require repeated or continuous treatment as the surface of the particle is dissolved and new metal oxides are exposed.

The preferred embodiment of the liquid chromatography system of the present invention utilizes methods to minimize the exposure of all process solution-contacting surfaces to oxygen. Dissolved oxygen within the mobile phase, for example, can react with exposed metals on these surfaces to form oxides which will interfere with the MIPC chromatographic separation. The liquid chromatography system preferably employs a degassing method for essentially removing dissolved oxygen from the mobile phase prior to contact with the rest of the chromatography system. Examples of degassing methods include sparging of the mobile phase with an inert gas such as argon or helium, or filtering the mobile phase under vacuum. A preferred method uses a vacuum type degasser which employs inline passage of the mobile phase over one side of an oxygen permeable membrane system where the other side is subjected to a vacuum. An example of a suitable four channel vacuum type degasser is Degaset™, Model 6324 (MetaChem Technologies, Torrance, Calif.).

In another embodiment of the invention, a stainless steel HPLC system can be used if a component for removing multivalent cations, herein referred to as a "multivalent cation capture resin," is also used. A multivalent cation capture resin is preferably a cation exchange resin or chelating resin. Any suitable cation exchange resin or chelating resin can be used. Preferred cation exchange and chelating resins are described below.

Cation exchange resins having an ion exchange moiety selected from the group consisting of iminodiacetate, nitriloacetate, acetylacetone, arsenazo, hydroxypyridinone, and 8-hydroxyquinoline groups are particularly preferred. Cation exchange resins having hydroxypyridinone groups are especially useful for removing iron from the system. Cation exchange resins having iminodiacetate groups are particularly preferred for use in the present invention because of their wide availability in resin format.

A chelating (i.e., coordination binding) resin is an organic compound which is capable of forming more than one non-covalent bond with a metal. Chelating resins include iminodiacetate and crown ethers. Crown ethers are cyclic oligomers of ethylene oxide which are able to interact strongly with alkali or alkaline earth cations and certain transition metal cations. A cavity in the center of the molecule is lined with oxygen atoms which hold cations by electrostatic attraction. Each crown ether has a strong preference for cations whose ionic radius best fits the cavity.

The multivalent cation capture resin is preferably contained in a guard column, guard cartridge, or guard disk. Guard columns and cartridges are frequently used to protect liquid chromatography columns from contamination and are widely available. In their normal use, guard columns and cartridges typically contain packing material which is similar to the stationary phase of the separation column. However, for use in the present invention, the guard column or cartridge must contain a multivalent cation capture resin. The guard disc or guard column must contain beads in which the metal ions can be trapped, but where DNA cannot enter the bead and be trapped.

For use in the system of the present invention, the guard cartridge or 1 column should be sufficiently large to provide adequate capacity, but must be small enough to allow effective gradient elution to be used. A preferred guard cartridge has a void volume of less than 5 mL, more preferably, less than 1 mL, so that the mobile phase gradient is not delayed by more than 5 minutes and, preferably, less than 1 minute. The preferred cartridge has a 10×3.2 mm bed volume.

Guard disks are described in detail in U.S. Pat. No. 5,338,448, which is incorporated herein by reference in its entirety. For use in the present invention, a guard disk comprises a layer or pad of a multivalent cation capture resin which has been incorporated into a fabric or membrane so that the resin is not separable from the guard disk under liquid flow conditions present during the performance of chromatographic separations.

In its preferred form, the guard disk is circular, having a rigid annular outer ring or collar for easy handling. The annular ring can be constructed of any suitable material which is inert to the chromatographic separation, such as inert conventional engineering plastic. The only requirement for the material is that it must be inert to the mobile phase and sample and have sufficient dimensional stability. The rigid annular outer ring of the guard disk can comprise a single rigid annular outer ring encircling a disk-shaped pad of guard disk material. As used herein, the term "guard disk material" refers to a layer or pad of multivalent cation capture resin which has been incorporated into a fabric or membrane.

Figure 6A:
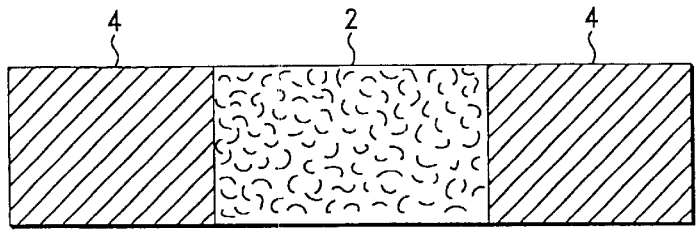
FIG. 6A shows a guard disk having a one-piece annular ring.

As shown in FIG. 6A, one or more pads of guard disk material 2 are placed in the rigid annular ring 4. For example, the fabric can be cut to a circular diameter which securely contacts the inner diameter surface of the annular ring. As the disk holder is tightened against the disk, the top and bottom surfaces of the holder seal against the collar of the guard disk. Sealing pressure from the guard disk holder is, therefore, applied against the collar of the disk which prevents the material of the guard disk pad from being crushed.

Figure 6B:
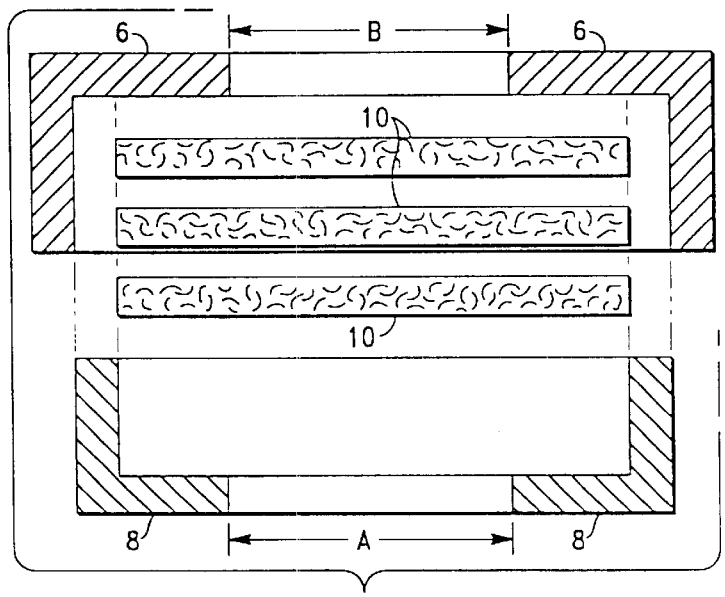
FIG. 6B is an exploded view of a guard disk having a two-piece annular ring and containing three pads of guard disk material (i.e., a layer or pad of multivalent cation capture resin which has been incorporated into a fabric or membrane).
Figure 6C:
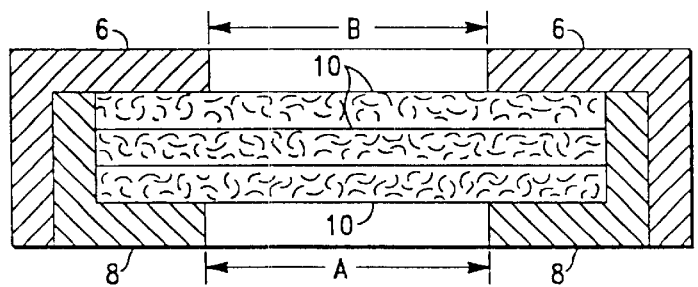
FIG. 6C shows an assembled view of the guard disk of FIG. 6B.

Alternatively, the rigid annular outer ring can comprise two flanged rings, as shown in FIGS. 6B and 6C, an outer flanged ring 6 and an inner flanged ring 8, where the inner flanged ring is insertable within the flange of the outer ring, forming a press-fit two-piece collar around one or more pads of guard disk material 10. Preferably, the inner diameter (a) of the inner flanged ring will have the same diameter as the separation column bed.

In the two-piece annular ring embodiment shown in FIG. 6C, one or more pads of guard disk material 10 having a diameter greater than the inner diameter (b) of the outer flanged ring 6 are positioned within the flanges of the outer ring. The inner flanged ring 8 is then inserted into the outer ring to form a press-fit two-piece annular ring in which the guard disk pad(s) is (are) frictionally held within the press-fit ring or collar. Preferably, the inner diameter (b) of the outer flanged ring and the inner diameter (a) of the inner flanged ring are substantially the same.

Alternatively, the rigid annular outer ring can be incorporated into the guard disk holder or chromatographic column cap. The annular ring is a flange that is part of one or both sides of the disk holder or the column cap. In this case, the guard disk does not have an outer ring. A circle of the guard disk sheet material is placed into the holder or column cap. The flange in the holder column cap is annular so that, when the holder or column cap is tightened, the flange pinches or seals the outer annular portion of the guard disk. The center portion of the guard disk not pinched is in a chamber or depression in the holder or cap. Fluid flows through the center portion, allowing the guard disk to retain particulate or strongly adsorbed material, but fluid cannot flow around the disk or past the edges. The function of the guard disk is exactly the same as when the collar is part of the guard disk itself. However, in this case, the collar is part of the holder or column cap.

In the system of the invention, a multivalent cation capture resin contained in a guard column, guard cartridge, or guard disk is placed upstream of the separation column. Preferably, the guard column, cartridge, or disk containing the resin is placed upstream of the sample injection valve. Although this is preferably a guard disk, a guard cartridge or column can be used as long as the dead volume of the cartridge or column is not excessive and an effective mobile phase gradient can be produced.

Additionally, a second guard disk, column, or cartridge can be placed between the sample injection valve and the separation column. In certain cases, the second guard disk (or cartridge or column) can be avoided if the contaminants are sufficiently cleaned by a guard column placed upstream of the injection valve, or if the contaminants are avoided through the use of nonmetal or titanium components throughout the HPLC system.

Figure 7:
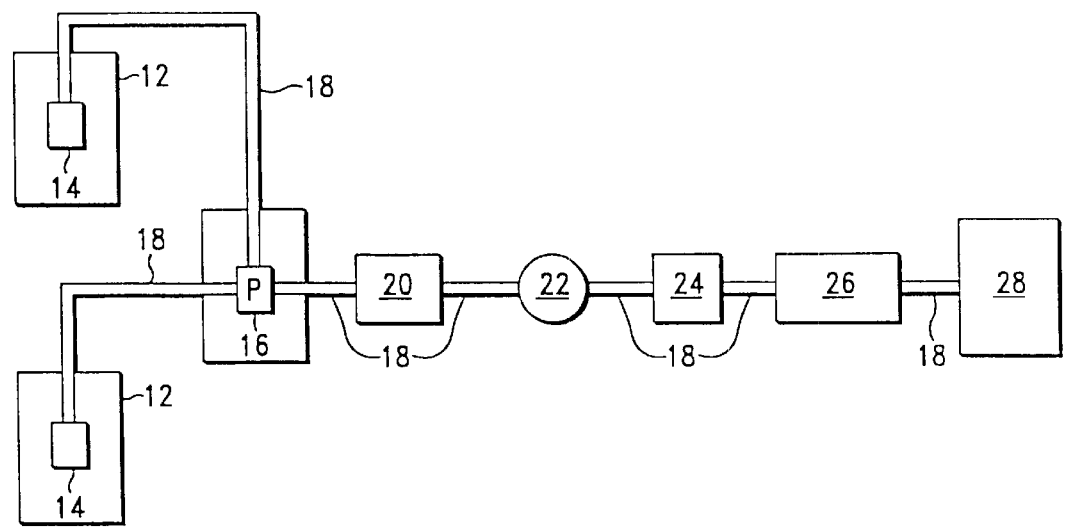
FIG. 7 shows placement of a chelating guard column and chelating guard disk in a liquid chromatographic system for polynucleotide separation.

Placement of a chelating guard column and chelating guard disk in a liquid chromatography system for polynucleotide separation is illustrated in FIG. 7. The mobile phase reservoirs 12 contain mobile phase inlet filters 14 which are connected to the solvent pump 16 by system tubing 18. The solvent pump 16 is connected to a chelating column 20 by system tubing 18. The chelating column 20 is connected to the sample injection valve 22 by system tubing 18. The sample injection valve has means for injecting a sample (not shown). The sample injection valve 22 is connected to a chelating guard disk 24 by system tubing 18. The chelating guard disk 24 is connected to the inlet (not shown) of the separation column 26 by system tubing 18. Detector 28 is connected to the separation column 26. As discussed above, the system tubing, mobile phase inlet filters, solvent pump, sample injection valve, and separation column are preferably made of titanium, coated stainless steel, or organic polymer. The material is preferably treated so that it does not release multivalent cations. The treatment can include treatment with nitric acid, phosphoric acid, pyrophosphoric acid, or chelating agents. In cases, where components of the HPLC do not release metal ion contaminants and are suitable for MIPC, then use of the chelating cation exchange guard column or guard disc is not necessary.

In operation, mobile phase from the mobile phase reservoirs 12 is pumped through mobile phase inlet filters 14 by solvent pump 16. By way of system tubing 18, the mobile phase stream flows through chelating column 20, through sample injection valve 22, through chelating guard disk 24, then into separation column 26. Detector 28 is located downstream from separation column 26.

FIG. 8 illustrates a specific embodiment of the invention in which a chelating guard disk is placed in direct contact with a titanium frit at the top portion of a chromatographic separation column. Column top 30 has conventional fittings for receiving mobile phase and sample through inlet tubing 32. The column top or cap 30 is fitted and sealably attached to column body 34 containing chromatographic bed 36 using a conventional fitting 38 (e.g., threaded) or any equivalent fitting capable of tightly sealing the column top to the column body. The column top 30 is adapted to receive the chelating guard disk 40 in a sealing cavity 42. In this embodiment, the guard disk 40 is in direct contact with a titanium column frit 44, which is located at the upstream end of the column body 34 to prevent disturbance of the chromatographic bed 36 when the column top 30 is removed to observe the guard disk.

In operation, solvent pump 46 pumps elution solvent to sample injection valve 48 into column top 30 through chelating guard disk 40 and then through titanium frit 44 before entering chromatographic bed 36. Mobile phase pressure upstream from the guard disk is measured by pressure transducer 50 which is electrically connected to a display device 52.

As discussed above, a chelating guard column, cartridge, or disk can be used in conjunction with a conventional, stainless steel liquid chromatography system, or with a system containing non-metal or titanium components in order to provide extra protection against ionic contaminants. For additional column protection, a mobile phase containing 0.1 mM tetrasodium EDTA or other chelating solution can be used during the performance of polynucleotide separations.

The methods of the invention comprise using the improved systems described above to separate mixtures of polynucleotide fragments, particularly double-stranded polynucleotide fragments. The methods of the present invention can be used to separate polynucleotide fragments having up to about 1500 base pairs using MIPC and up to about 20,000 base pairs using slalom chromatography.

In most cases, the method will be used to separate polynucleotides having 80 or more base pairs, up to about 1500 base pairs. The method provides good separation and reliability for longer polynucleotides having base pairs within the range of 10–100, but is also useful for base pairs less than 10.

The polynucleotides which can be separated by the present method include double-stranded polynucleotides. Since the mechanism of the degradation effect is still unknown, it is not known how significantly single-stranded polynucleotide separations are affected. Furthermore, only short (25-mer) single-stranded polynucleotides are usually separated by liquid chromatographic methods. With short lengths, the effect is more difficult to detect.

Samples containing mixtures of polynucleotides can result from total synthesis of polynucleotides, cleavage of DNA with restriction endonucleases or RNA, as well as polynucleotide samples which have been multiplied or amplified using polymerase chain reaction (PCR) techniques or other amplifying techniques. Also, the separations of polynucleotides can be performed at different temperatures. As the temperature of the column is increased, heteroduplexes that may be present in the samples will partially melt and elute earlier than homoduplexes in the sample. The separation is carried out under conditions effective to at least partially denature the heteroduplexes (e.g. thermal or chemical denaturing) resulting in the separation of the heteroduplexes from the homoduplexes. Under these conditions, the homoduplexes are eluted under size dependent conditions, or at higher temperatures, size and sequence dependent conditions, and the heteroduplexes are separated under size and sequence dependent conditions (P. Underhill, *Proc. Natl. Acad. Sci.* 93:196–200 (1996)).

The systems of the present invention are preferably used to separate double-stranded polynucleotide fragments by MIPC. The preferred method is described by Bonn et al. in U.S. Pat. No. 5,585,236, which is incorporated herein by reference in its entirety. The method of Bonn et al. utilizes separation columns filled with nonporous polymeric beads having an average diameter of about 1–100 microns, preferably 1–10 microns, more preferably 1–5 microns. Beads having an average diameter of 1.5–3.0 microns are most preferred.

The nonporous polymeric beads are prepared by a two-step process in which small seed beads are initially produced by emulsion polymerization of suitable polymerizable monomers. The emulsion polymerization procedure of the invention is a modification of the procedure of J. W. Goodwin et al. (*Colloid & Polymer Sci.*, 252:464–471 (1974)). Monomers which can be used in the emulsion polymerization process to produce the seed beads include styrene, alkyl substituted styrenes, alpha-methyl styrene, and alkyl substituted alpha-methyl styrenes, preferably monomers where the benzene-type ring is substituted with 1–4 $C_{1-6}$ alkyl groups, and the monomers described, for example, in U.S. Pat. No. 4,563,510. The seed polymer beads are then enlarged and alkylated, as described by Bonn et al. in U.S. Pat. No. 5,585,236.

In MIPC, the polynucleotides are matched with a counter ion agent and then subjected to chromatography using the alkylated beads described above. The identity of the counter ion agent can be varied and conventional agents capable of forming ion pairs with polynucleotides can be used. Typical counter ion agents include trialkylammonium salts of organic or inorganic acids, for example, trimethyl, triethyl, tripropyl, and tributyl ammonium acetates, halides, etc. A particularly preferred counter ion agent is triethylammonium acetate (TEAA). Tetraalkylammonium salts have also been used such as (25 mM) tetrabutylammonium bromide.

To achieve high resolution chromatographic separations of polynucleotides, it is generally necessary to tightly pack the chromatographic column with the solid phase polymer beads. Any known method of packing the column with a column packing material can be used to obtain adequate high resolution separations. Typically, a slurry of the alkylated polymer beads is prepared using a solvent having a density equal to or less than the density of the polymer beads. The column is then filled with the polymer bead slurry and vibrated or agitated to improve the packing density of the polymer beads in the column. Mechanical vibration or sonication are typically used to improve packing density.

For example, to pack a column having an inner diameter of 50×4.6 mL, 1.4 grams of alkylated beads are suspended in 15 mL of tetrahydrofuran with the help of sonication. The suspension is then packed into the column using 50 mL of methanol at 70 MPa of pressure. In the final step, the packed bed is washed with 50 mL of deionized water. This reduces the swelling of the beads and improves the density of the packed bed.

Alternatively, slalom chromatography can be used to separate larger DNA fragments (i.e., 5000 or more base pairs) according to the methods of the invention. Slalom chromatography, as described by J. Hirabayashi et al. (*Anal. Biochem.*, 178:336–341 (1989); *Biochemistry*, 29:9515–9521 (1990)), is a method of separating DNA fragments having dimensions comparable to the chromatographic particles. In practice, this means that currently available columns separate fragments in the range of 5000–50,000 base pairs. Fragments are eluted in order of size, with the smallest fragments eluting first, opposite to the order of gel permeation. The mechanism is believed to be hydrodynamic sieving, rather than surface interactions between the DNA and the chromatographic packing. Particle size and mobile phase flow rate have the greatest influence on separation. While the mobile phase is usually aqueous buffer, organic or aqueous organic mobile phases are not excluded.

In slalom chromatography, the chromatographic separation column is packed with "slalom chromatography DNA separation particles". The term "slalom chromatography DNA separation particles" refers to any material which is capable of separating DNA fragments by slalom chromatography. Slalom chromatography separation particles can be inert organic polymers, inert inorganic polymers, silica, or cation exchange resin. The only requirement for the slalom chromatography DNA separation particles is that they must have little interaction with the DNA fragments.

Procedures described in the past tense in the examples below have been carried out in the laboratory. Procedures described in the present tense have not been carried out in the laboratory, and are constructively reduced to practice with the filing of this application.

EXAMPLE 1

Sodium chloride (0.236 g) was added to 354 mL of deionized water in a reactor having a volume of 1.0 liter. The reactor was equipped with a mechanical stirrer, reflux condenser, and a gas introduction tube. The dissolution of the sodium chloride was carried out under inert atmosphere (argon), assisted by stirring (350 rpm), and at an elevated temperature (87° C.). Freshly distilled styrene (33.7 g) and 0.2184 g of potassium peroxodisulfate ($K_2S_2O_8$) dissolved in 50 mL of deionized water were then added. Immediately after these additions, the gas introduction tube was pulled out of the solution and positioned above the liquid surface. The reaction mixture was subsequently stirred for 6.5 hours at 87° C. After this, the contents of the reactor were cooled down to ambient temperature and diluted to a volume yielding a concentration of 54.6 g of polymerized styrene in 1000 mL volume of suspension resulting from the first step. The amount of polymerized styrene in 1000 mL was calculated to include the quantity of the polymer still sticking to the mechanical stirrer (approximately 5–10 g). The diameter of the spherical beads in the suspension was determined by light microscopy to be about 1.0 micron.

Beads resulting from the first step are still generally too small and too soft (low pressure stability) for use as chromatographic packings. The softness of these beads is caused by an insufficient degree of crosslinking. In a second step, the beads are enlarged and the degree of crosslinking is increased. The protocol for the second step is based on the activated swelling method described by Ugelstad et al. (*Adv. Colloid Interface Sci.*, 13:101–140 (1980)). In order to initiate activated swelling, or the second synthetic step, the aqueous suspension of polystyrene seeds (200 mL) from the first step was mixed first with 60 mL of acetone and then with 60 mL of a 1-chlorododecane emulsion. To prepare the emulsion, 0.206 g of sodium dodecylsulfate, 49.5 mL of deionized water, and 10.5 mL of 1-chlorododecane were brought together and the resulting mixture was kept at 0° C. for 4 hours and mixed by sonication during the entire time period until a fine emulsion of <0.3 microns was obtained. The mixture of polystyrene seeds, acetone, and 1-chlorododecane emulsion was stirred for about 12 hours at room temperature, during which time the swelling of the beads occurred. Subsequently, the acetone was removed by a 30 minute distillation at 80° C. Following the removal of acetone, the swollen beads were further grown by the addition of 310 g of a ethyidivinylbenzene and divinylbenzene (DVB) (1:1.71) mixture also containing 2.5 g of dibenzoylperoxide as an initiator. The growing occurred with stirring and with occasional particle size measurements by means of light microscopy.

After completion of the swelling and growing stages, the reaction mixture was transferred into a separation funnel. In an unstirred solution, the excess amount of the monomer separated from the layer containing the suspension of the polymeric beads and could thus be easily removed. The remaining suspension of beads was returned to the reactor and subjected to a stepwise increase in temperature (63° C. for about 7 hours, 73° C. for about 2 hours, and 83° C. for about 12 hours), leading to further increases in the degree of polymerization (>500). The pore size of beads prepared in this manner was below the detection limit of mercury porosimetry (<30 Å).

After drying, the dried beads (10 g) from step two were suspended in 100 mL of 1-chlorododecane and stirred (370 rpm) for 12 hours at 100° C. following addition of 1 g of aluminum chloride. At the end of this period, the reaction mixture was cooled to 80° C. and mixed with 150 mL of 4M hydrochloric acid. After 2 minutes of stirring, the reaction mixture, now containing hydrochloric acid, was transferred into a separation funnel and overlaid by 300 mL of n-heptane. The phases were stirred into each other and, after subsequent separation of phases, the aqueous phase was removed and discarded. The remaining organic phase was washed two additional times with 200 mL of 1M hydrochloric acid and subsequently centrifuged at 5000 rpm. The separated beads were washed four times with 100 mL of n-heptane, and then two times with each of the following: 100 mL of diethylether, 100 mL of dioxane, and 100 mL of methanol. Finally, the beads were dried.

Alternatively, the alkylation was carried out using tin chloride by means of a procedure which is otherwise similar to that utilizing aluminum chloride. One hundred mL (100 mL) of 1-chlorooctadecane, 10 g of poly(styrene/ethylstyrene/divinylbenzene) beads, and 5 mL of $SnCl_4$ were stirred at 100° C. for 12 hours. The mixture was cooled to room temperature, 100 mL of n-heptane was added and the mixture was then extracted with 4×300 mL of water in a separation funnel. Subsequent centrifugation was carried out for 5 minutes at 5000 rpm. The supernatant and 1-chlorooctadecane were discarded and water was removed as completely as possible. Washing with 2×150 mL of n-heptane, 2×150 mL of dioxane, and 2×150 mL of methanol completed the procedure. Each of the washing steps was followed by centrifugation at 5000 rpm. The alkylated beads were then dried at 60° C.

Alkylation of the aromatic rings of the polymer was verified by Fourier Transform Infrared spectroscopy (FTIR). The beads differed only slightly in size from each other. The mean value for the particle diameter was found to be 2.10 microns, with a standard deviation of 0.12 micron.

The beads preferably are subjected to an acid wash treatment in order to essentially eliminate multivalent cation contaminants. The beads prepared are washed three times with tetrahydrofuran and two times with methanol. Finally the beads are stirred in a mixture containing 100 mL tetrahydrofuran and 100 mL concentrated hydrochloric acid for 12 hours. After this acid treatment, the polymer beads are washed with a tetrahydrofuran/water mixture until neutral (pH=7). The beads are then dried at 40° C. for 12 hours.

The separation of single- and double-stranded DNA was accomplished using MIPC. Triethylammonium acetate was used as the counter ion agent. Elution was effected with the help of a linear organic solvent gradient of acetonitrile. The chromatographic conditions were as follows: Column: 50×4.6 cm i.d. Mobile phase: 0.1 M TEAA, pH 7.0. Gradient: 7.5–13.75% acetonitrile in 4 minutes, followed by 13.75–16.25% acetonitrile in 6 minutes. Flow rate: 1 mL/min. Column temperature: 50° C. Detection: UV at 254 nm. Sample: 0.5 µg pBR322 DNA-Hae III restriction digest.

EXAMPLE 2

Seed polystyrene latex was prepared using 0.374 g of NaCl, 0.1638 g of $K_2S_2O_8$, 404 mL of water, and 37 mL of styrene, stirred at 81° C. at 350 rpm for 6 hours. The resulting seed particles had a diameter of 1.3 microns. Then, 200 mL of the seed latex was swollen with a mixture of 50 mL of divinylbenzene, 0.5 mL of dibenzoylperoxide, and 5 mL of acetone. The mixture was stirred for 6 hours at 40° C. and 1 hour at 45° C. The final diameter of the particles was 1.8 microns. Next, the excess divinylbenzene was removed and the particles polymerized for 12 hours at 65° C., followed by 14 hours at 85° C. After drying, alkylating, and cleaning, the polymer was used as described in Example 1.

EXAMPLE 3

Many experiments in molecular biology, including hybridization and DNA sequencing, require tagging of DNA with either radioactive isotopes, such as $^{32}P$ or $^{33}P$ or fluorescent dyes, such as fluorescein, 2',7'-dimethyoxy-4',5'-dichlorofluorescein, tetramethylrhodamine, and rhodoamine, as described by S. Fung et al. (U.S. Pat. No. 4,855,225). Since the covalent coupling of radioisotopes and fluorescent dyes is usually incomplete, labeled DNA must be purified away from unreacted DNA, which otherwise will compete with the dye-labeled primers and probes in sequencing and hybridization reactions.

The purification of labeled samples was accomplished simply and rapidly by means of MIPC on nonporous, alkylated ($C_{18}$) poly(ethylvinylbenzene-divinylbenzene) beads. Recovery of DNA was at least 96%.

The separation of fluorescent dye-labeled DNA from unreacted DNA can also be achieved by reverse phase chromatography only, i.e., in the absence of a counter ion reagent, because the hydrophobic nature of the fluorophore significantly increases the retention of the DNA on an alkylated stationary phase relative to unreacted DNA. This is an example of separation based on polarity of the fragments.

EXAMPLE 4

If the gradient delay volume is minimized, the separation of PCR products and hybrid DNA derived from various sources of DNA, including living and dead organisms (animal and plant), as well as parts of such organisms (e.g., blood cells biopsies, sperm, etc.), on octadecyl-modified, nonporous poly-(ethylvinylbenzene-divinylbenzene) beads can be achieved with run times under 2 minutes.

The analysis of PCR products and hybrid DNA usually requires only separation and detection of one or two species of known length. Because of this, the resolution requirements are considerably less severe than for separations of DNA restriction fragments. Such less stringent resolution requirements allow the utilization of steep gradients and, consequently, lead to still shorter run times. The recovery rate for a polynucleotide fragment containing 404 base pairs was about 97.5%.

Unlike capillary electrophoresis (CE), PCR samples do not have to be desalted prior to analysis by MIPC. This represents a decisive advantage of MIPC over CE. With MIPC, it is thus possible to achieve a fully automated analysis of PCR samples if an automatic autosampler is utilized. Moreover, since the volume of sample injection is known, in contrast to CE, quantitation over several orders of magnitude can be achieved without the need for an internal standard, hence allowing the quantitation of gene expression, as well as the determination of virus titers in tissues and body fluids. A fully automated version of the method of the invention has been used to discriminate (i.e., distinguish) normal from mutated genes, as well as to detect oncogenes and bacterial and viral genome DNA (hepatitis C virus, HIV, tuberculosis) for diagnostic purposes. Moreover, adjustment of column temperature allows the stringency of hybridization reactions to be modulated.

PCR methods and processes have been described by R. K. Sreke et al. (*Science*, 230:1350–1354 (1985)) and K. B. Mullis (U.S. Pat. No. 4,683,202). These references are incorporated herein by reference for a more complete description of methods and processes for obtaining PCR samples which can be separated using the method of the present invention.

EXAMPLE 5

A Hewlett-Packard HP1090 instrument formerly used for protein separations was purchased and outfitted with a column and mobile phases as described in Examples 1 and 2. In this case, the column contained 0.5 µm 316 stainless steel frits. The HP1090 instrument is available only as a stainless steel instrument.

Figure 2:
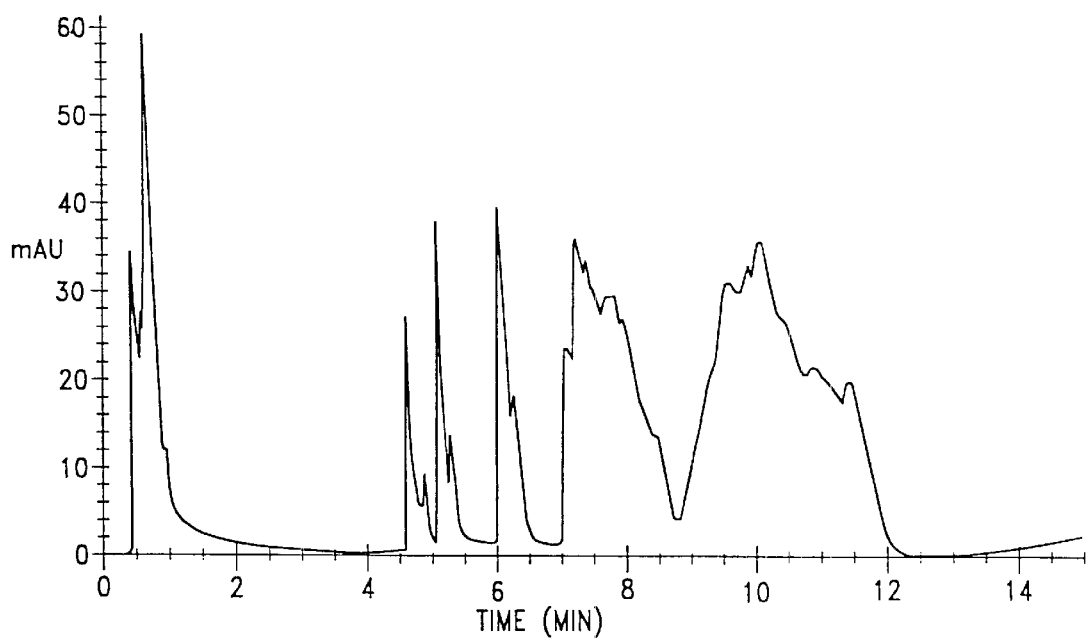
FIG. 2 shows further contamination and degradation of the HPLC separation now affecting all dsDNA fragments down to 80 base pairs, with the larger fragments being affected the most.
Figure 3:
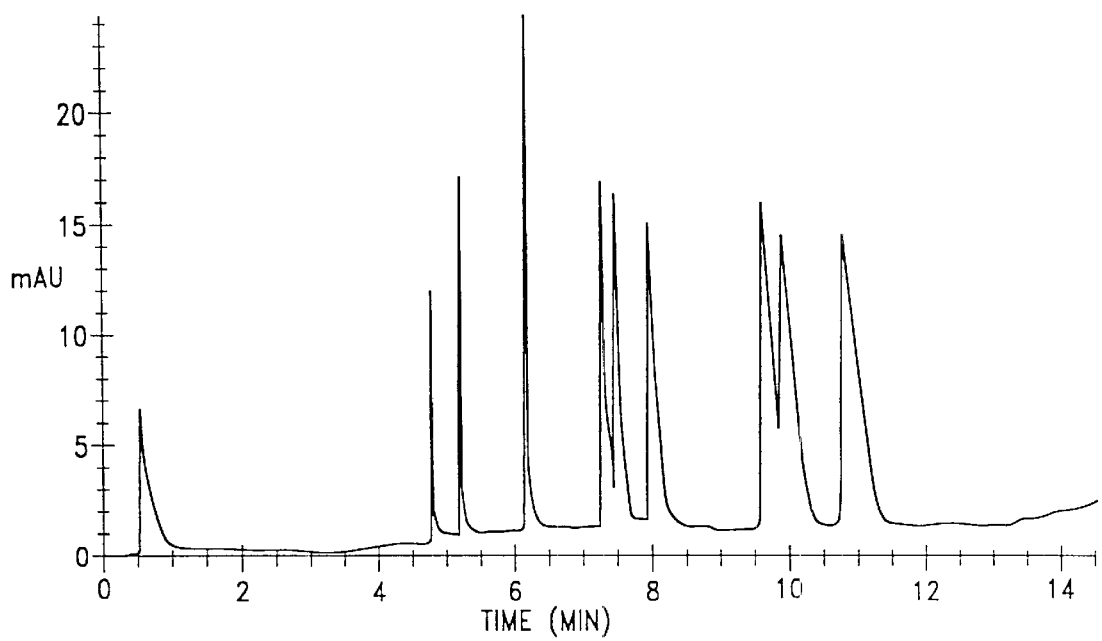
FIG. 3 shows a chromatogram of dsDNA separation following injection of the column with tetrasodium EDTA, a metal chelating agent.
Figure 4:
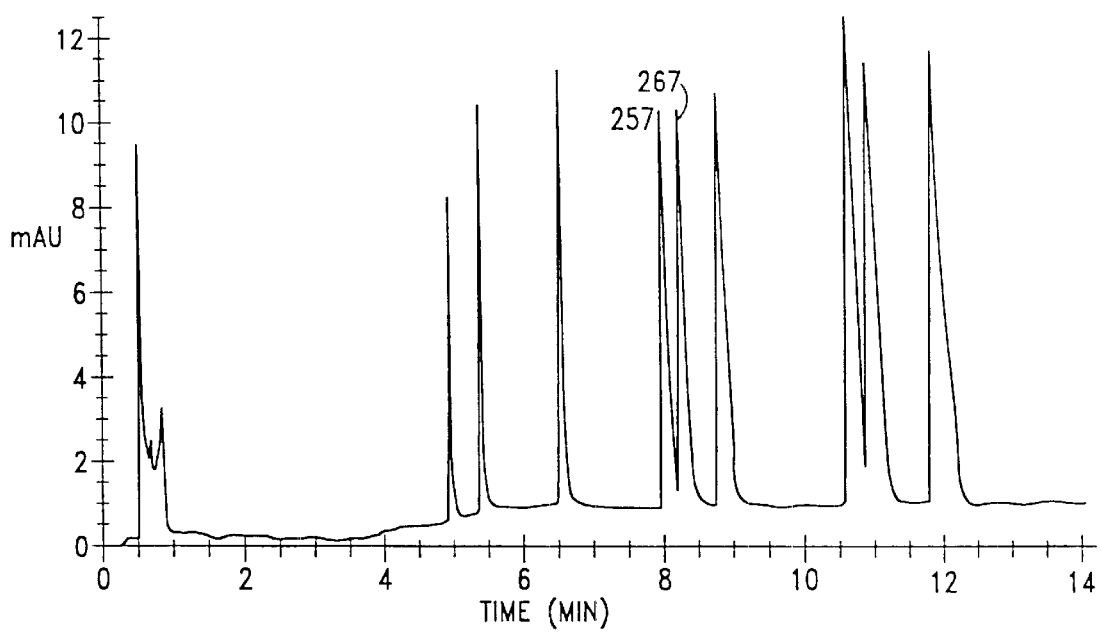
FIG. 4 shows a chromatogram of dsDNA separation obtained when a guard disk containing gel-type iminodiacetate was positioned directly in front of the sample injection valve of the HPLC system.
Figure 5:
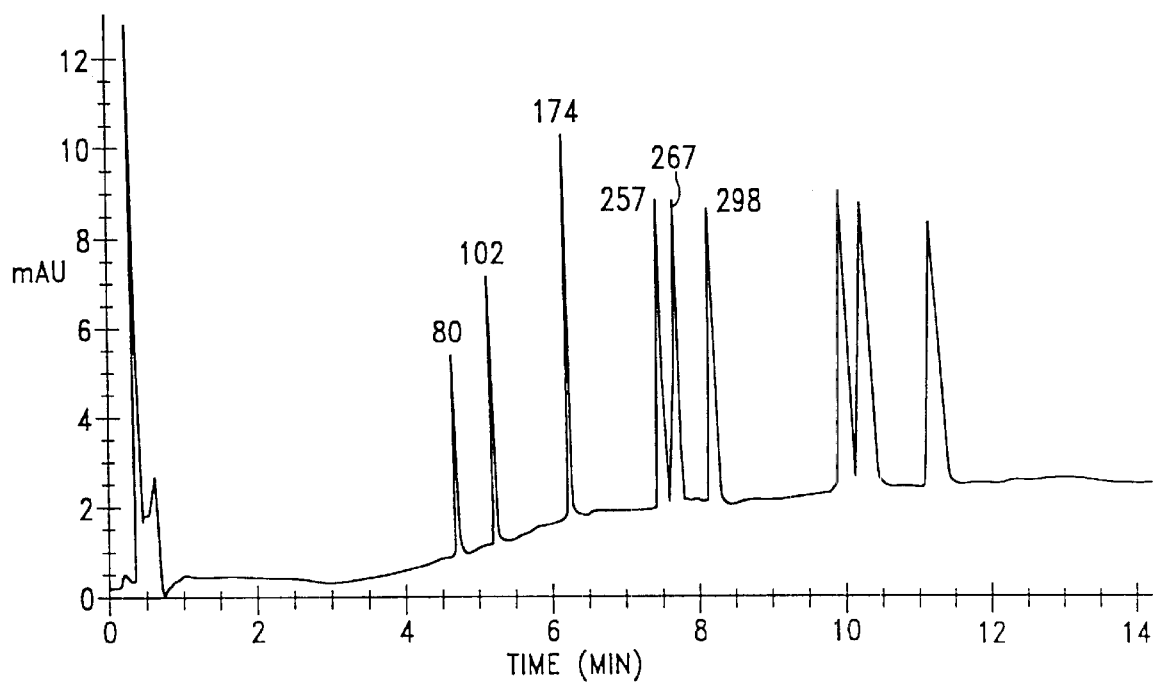
FIG. 5 shows a chromatogram of dsDNA separation obtained when a guard disk containing gel-type iminodiacetate was placed directly in front of the separation column of the HPLC system (i.e., between the sample injection valve and the separation column).

The separation of a DNA standard resulted in inconsistently degraded performance, as shown in FIGS. 1 and 2. Then, 0.1 mM tetrasodium EDTA was added to mobile phases A and B. While this improved performance, degradation of the column still occurred after one day of use.

The instrument was then outfitted with a column containing 0.5 µm titanium frits and an iminodiacetate guard disk positioned in front of the column. This modification resulted in several days of separation with no degradation of performance.

Later, a guard cartridge with dimensions of 10×3.2 mm, containing iminodiacetate chelating resin of 2.5 mequiv/g capacity and 10 µm particle size was positioned directly in front of the injection valve. This also resulted in elimination of the contamination problem. The system was able to operate with or without the guard disk in this mode.

The minimum modifications needed to practice the invention to achieve improved polynucleotide separations involve using a stainless steel HPLC system that has been retrofitted with a chelating disk or cartridge positioned in front of the injection valve or column and a column containing titanium or PEEK frits. Newer HPLC equipment might be able to operate with only changing the critical frits to titanium or PEEK and then preventing further corrosion of the instrument with degassing of the mobile phase.

While the use of tetrasodium EDTA by itself is not always adequate, its use can degrade performance if the concentration is high and the EDTA contributes to the driving ion action in the MIPC separation. EDTA can also interfere with detection by mass spectrometry, or can interfere with the subsequent analysis of collected fractions.

The performance of any column capable of separating DNA can be improved through the column protection methods and system described in this example. Other columns that have been used to separate double-stranded DNA include nonporous alkylated reverse phase silica materials, large pore poly(styrene/divinylbenzene) and other polymeric materials, and large pore silica-based reverse phase materials.

EXAMPLE 6

The column material described in Example 5 is packed in column body hardware consisting of titanium, PEEK, or other polymeric material, and the column frits are titanium, PEEK, or other polymeric material. The HPLC system still requires minimum column protection, as described in Example 5, consisting of a chelating ion exchange resin positioned in front of the injection valve or in front of the column.

EXAMPLE 7

The performance of the HPLC system was improved by employing polymeric or titanium in all of the frits. In the case of a Hewlett-Packard HP1090 instrument, polymeric inlet mobile phase filters replaced the standard stainless steel filters. Titanium frits replaced the stainless steel frits used in the mixer after the pump head, but before the chelating ion exchange cartridge before the injector. This resulted in a several-week lifetime of the cartridges before breakthrough of contaminants occurred.

EXAMPLE 8

Alternatively, a PEEK or titanium HPLC system can be employed for double-stranded DNA separation. In this case, a column containing titanium frits or PEEK frits must be used. Column protection consisting of the chelating cartridge positioned before the injection valve and/or the guard disk positioned before the column is preferred, but not necessary. Mobile phase containing a chelating reagent is preferred, but not necessary, and is used only in cases where collection of the DNA is not required.

A Waters Action Analyzer was outfitted with a column, as described in Examples 1 and 2, containing 0.5 μm titanium frits. The HPLC instrument was a low-pressure mixing quaternary gradient system that contained polymeric inlet filters and PEEK pump heads, frits, and tubing. The inlet and outlet check valves were also PEEK, except for a ceramic seat and sapphire ball. A Waters 484 detector was used, with the detection wavelength set to 254 nm.

In this example, all of the flow paths were either titanium, sapphire, ceramic, or PEEK, except for the column body, which was 316 stainless steel. The 316 stainless steel body was passivated with dilute nitric acid prior to packing of the chromatographic material. The 316 stainless steel column body was preferred for use in this example because titanium column bodies were not available with smooth inside walls, and PEEK column bodies flexed during the packing process, leading to less efficient column beds.

EXAMPLE 9

The effect of acid wash treatment of the PEEK frits used in packing the column on the performance of the HPLC system was demonstrated in this example. Using the Waters Action Analyzer and a packed column having untreated PEEK frits (Part no. 7100-052-2, Isolation Technologies, Inc.), FIG. 9 (first injection) and FIG. 10 (fifth injection on the same column) show the high resolution separation of DNA restriction fragments using octadecyl modified, nonporous poly(ethylvinylbenzene-divinylbenzene) beads. The experiment was conducted under the following conditions: Column: 50×4.6 mm i.d.; mobile phase 0.1 M TEAA, pH 7.2; gradient: 35–55% acetonitrile in 3 min, 55–65% acetonitrile in 7 min, 65% acetonitrile for 2.5 min; 100% acetonitrile for 1.5 min. back to 35% in 1 min. The flow rate was 0.75 mL/min; detection UV at 260 nm; column temp. 53° C.; p=2200 psi. The sample was 5 μl (=0.20 μg pUC18 DNA-Hae III digest).

Figure 10:
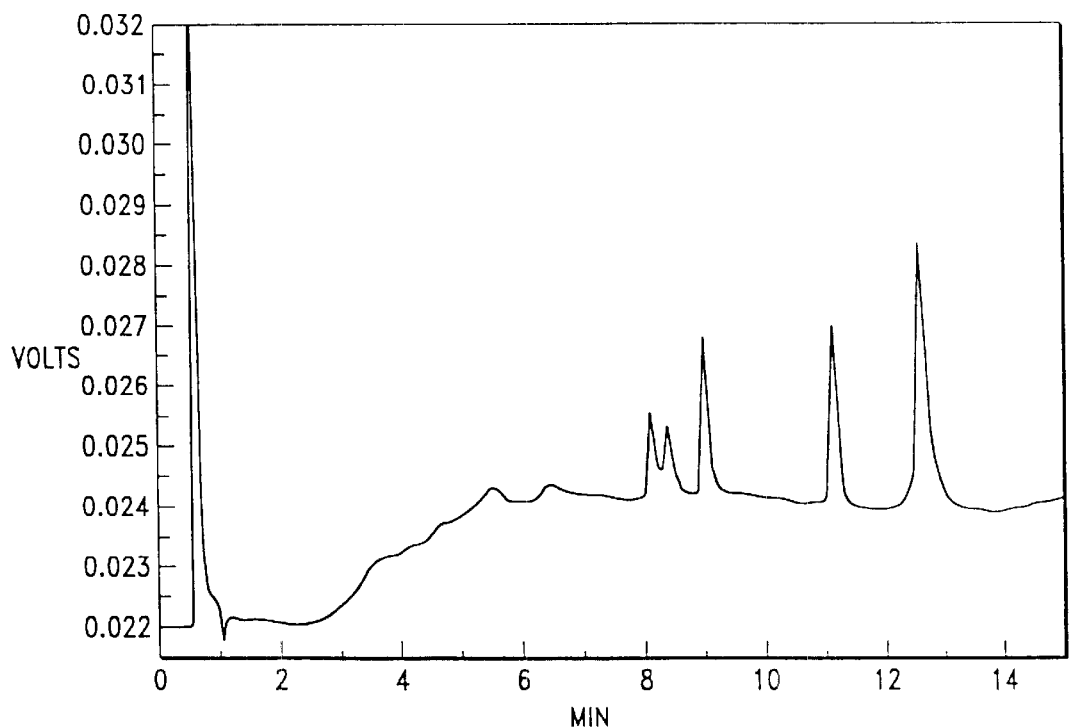
FIG. 10 shows the chromatogram from the fifth injection of DNA restriction fragments using the column of FIG. 9.
Figure 11:
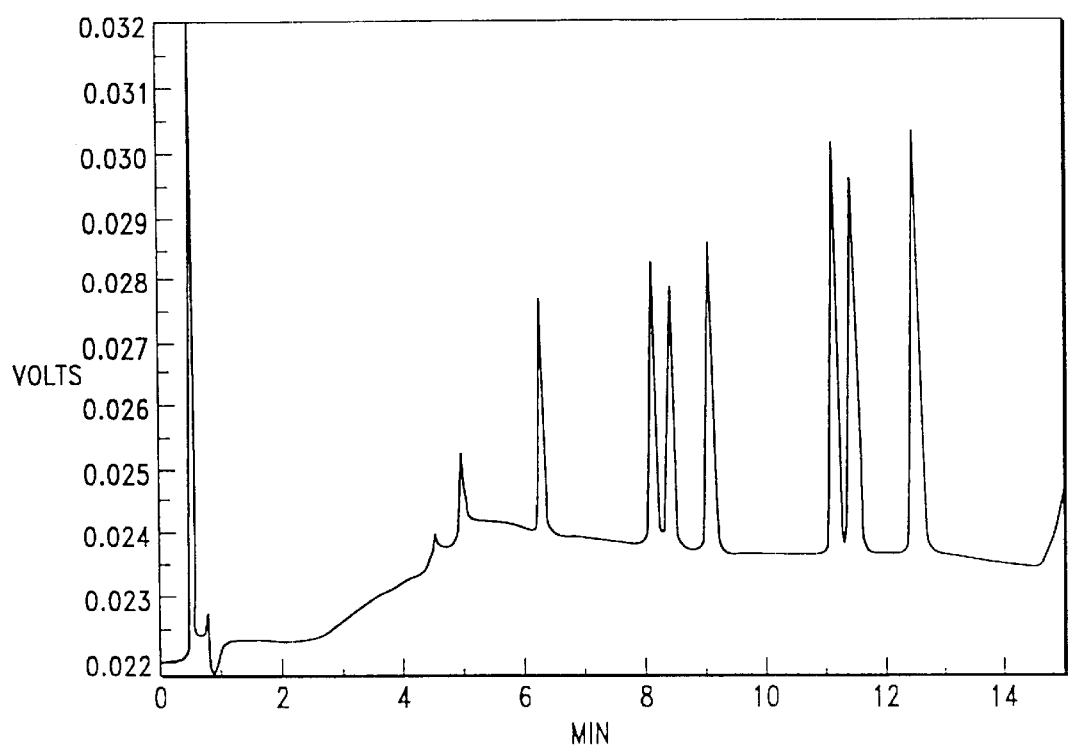
FIG. 11 shows a separation performed as in FIG. 9 but using a column having the same frits that were used in the column of FIG. 10 but which had been subjected to a nitric acid wash treatment.

The PEEK frits from the column used in FIG. 10 were removed and subjected to an acid wash treatment consisting of sonication in 30% nitric acid for about 60 min, followed by sonication in distilled water until pH=7. The separation procedure was repeated using these acid washed frits and, as shown in FIG. 11, this led to a major improvement in separation performance although the intensity of the 80 bp and the 102 bp fragments was still not satisfactory. As seen in other examples, the degradation of the separation was apparent for the smaller fragments rather than the larger fragments. In addition, this degradation appeared to be sequence dependent. Fragments with base pair size 267 and 458 were smaller than expected relative to fragments eluting immediately prior to and after these fragments. These data suggest that although metal ion contamination is a factor, there may be more than one mechanism for metals to interfere in MIPC.

Figure 12:
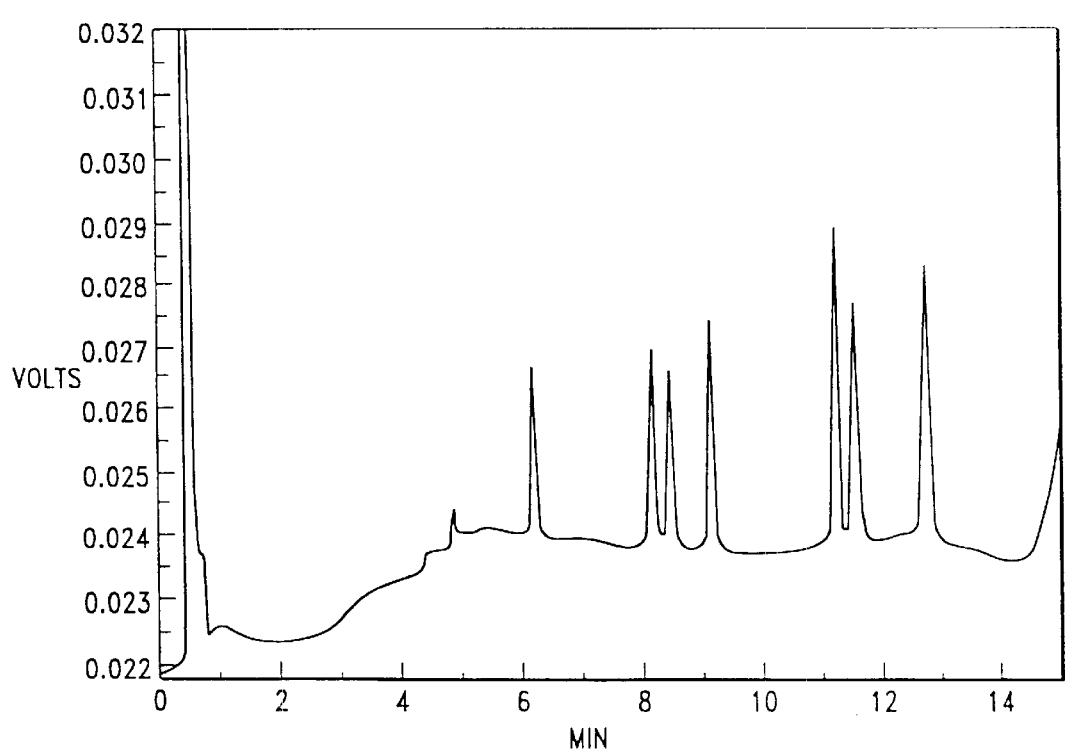
FIG. 12 shows a separation performed as in FIG. 9 but using a column having the same frits that were used in the column of FIG. 11 but which had been subjected to an acid wash treatments with $HNO_3$ and HCl.

For the chromatogram shown in FIG. 12, the separation procedure was repeated using PEEK frits which were washed using the following process: The frits from the column used to generate the chromatogram of FIG. 11 were subjected to an acid wash treatment consisting of sonication in 30% nitric acid for about 60 min, followed by sonication in distilled water until pH=7. These frits were then sonicated with HCl (36%) for about 5 minutes. The chromatogram in FIG. 12 was similar to that seen in FIG. 11.

Figure 9:
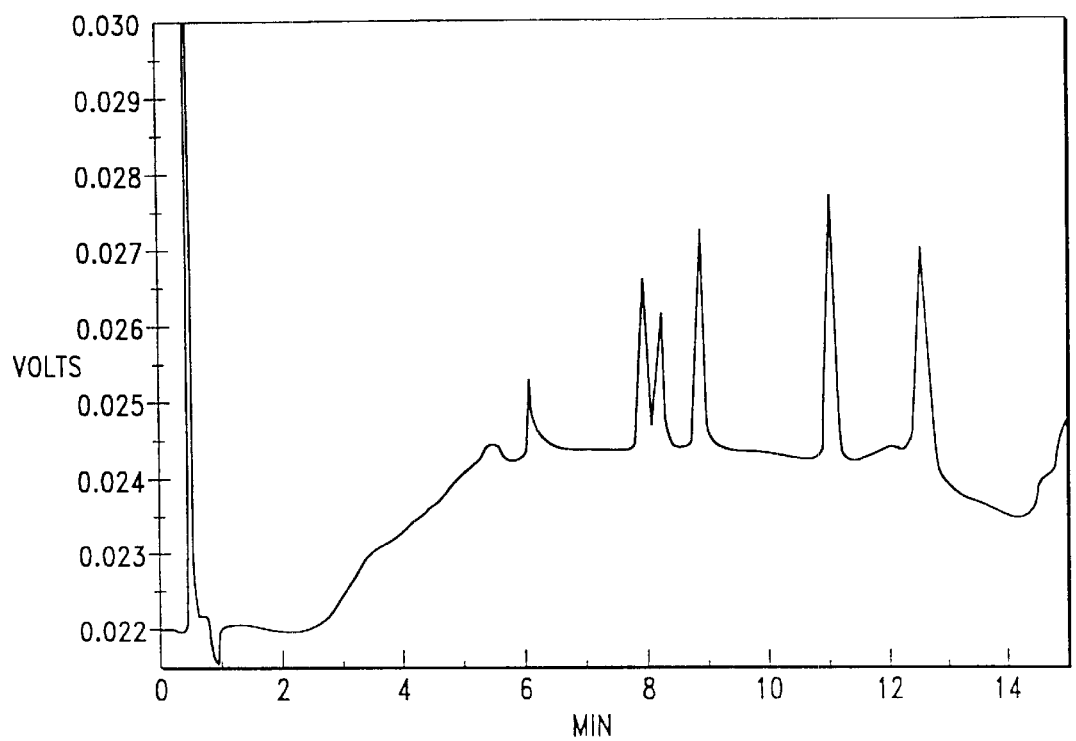
FIG. 9 shows a high resolution MIPC separation of DNA restriction fragments after the first injection of sample using a column having untreated PEEK frits.
Figure 13:
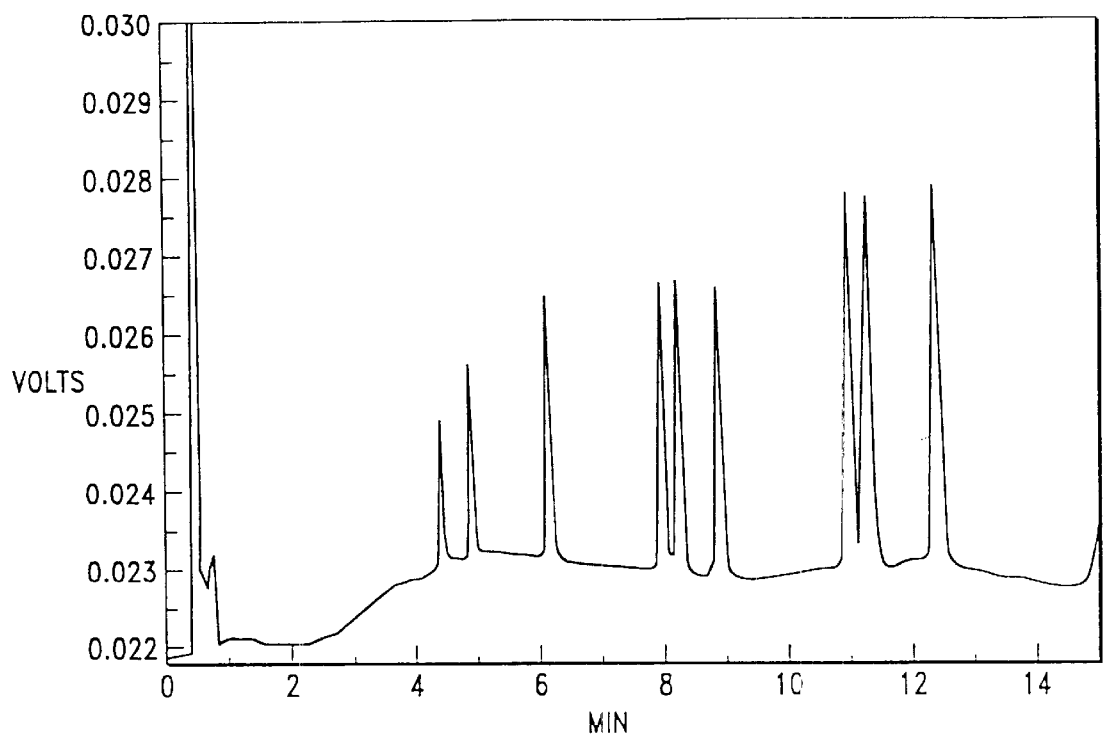
FIG. 13 shows a separation performed as in FIG. 9 but using a column having titanium frits.

The use of titanium frits (Isolation Technologies, Hopedale, Mass.) is shown in FIG. 13 where the separation conditions were the same as for FIG. 9.

Figure 14:
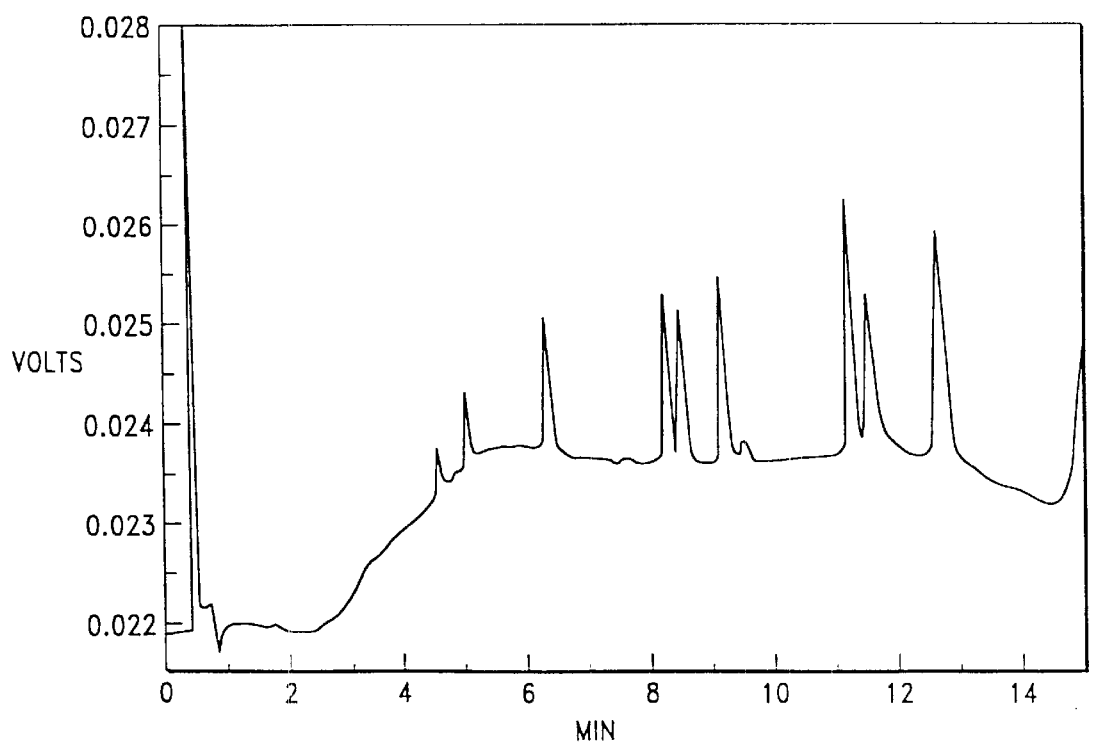
FIG. 14 shows a high resolution MIPC separation of DNA restriction fragments after the first injection of sample using a column having untreated PEEK frits.

In FIG. 14, the separation as carried out in FIG. 9 was repeated but using a new column packed using untreated PEEK frits from another source (Part no. A702, Upchurch Scientific, Oak Harbor, Wash.). The chromatogram in FIG. 14 shows the performance of these frits. Although the overall performance and especially the selectivity is almost identical to the separation shown in FIG. 13, one major difference can be detected in that the intensity of fragment 458 bp (peak #8) is clearly decreased.

EXAMPLE 10

The effect of acid wash treatment of the PEEK frits used in packing the column on the separation of single stranded DNA was demonstrated in this example. Using the Waters Action Analyzer and a packed column having titanium frits, FIG. 15 shows the high resolution separation of DNA restriction fragments using octadecyl modified, nonporous poly(ethylvinylbenzene-divinylbenzene) beads. The experiment was conducted under the following conditions: Column: 50×4.6 mm i.d.; mobile phase 0.1 M TEAA, pH 7.2; gradient: 20–80% acetonitrile in 16 min, 80–100% acetonitrile in 1.5 min, 100–20% acetonitrile in 1 min. The flow rate was 0.75 mL/min; detection UV at 260 nm; column temp. 51° C.; p=2200 psi. The sample was 5 μl (20-mer oligonucleotide).

Figure 17:
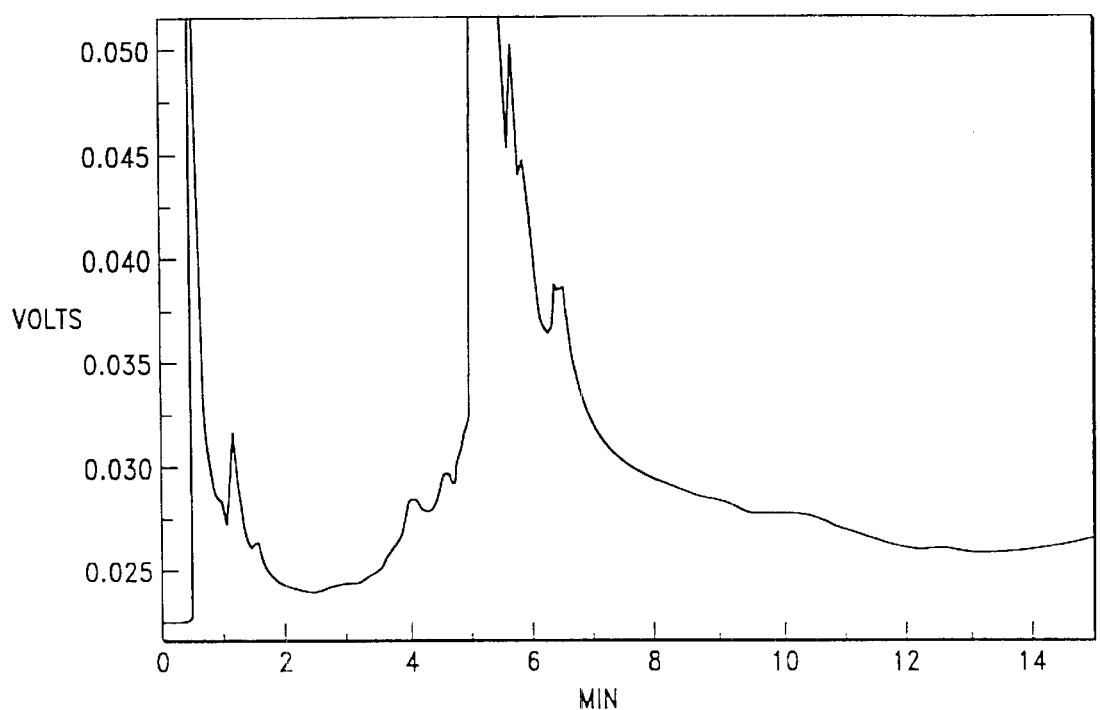
FIG. 17 shows separation of the oligonucleotide as used in FIG. 15 but on a column having PEEK frits which were treated with $HNO_3$ and HCl.

As shown in FIG. 15, the column was capable of resolving failure sequences very easily. When the same oligonucleotide was separated on a column having PEEK frits as shown in FIG. 16, the oligonucleotide still appeared at 6 minutes, but the separation performance was deteriorated. Almost all of the smaller peaks (failure sequences) have disappeared due to the influence of the PEEK frit. The performance of the oligonucleotide separation improved slightly, as shown in FIG. 17, when using a column having frits which were treated with $HNO_3$ and HCl.

Obviously, numerous modifications and variations of the present invention are possible in light of the above teachings. It is therefore to be understood that within the scope of the appended claims, the invention can be practiced otherwise than as specifically described herein.

All references cited herein are hereby incorporated by reference in their entirety.

What is claimed is:

1. A method for separating a mixture of polynucleotide fragments during passage through a liquid chromatographic column containing a separation bed comprising Matched Ion Polynucleotide Chromatography separation particles, wherein the method comprises:

supplying and feeding process solutions entering the column with components having process solution-contacting surfaces which contact process solutions held therein or flowing therethrough, wherein said process solution-contacting surfaces are material which does not release multivalent cations into aqueous solutions held therein or flowing therethrough, whereby the column is protected from contamination of the contents thereof by multivalent cations capable of interfering with polynucleotide separation, and wherein the polynucleotide fragments are separated by Matched Ion Polynucleotide Chromatography.

2. The method of claim 1 wherein said multivalent cations are capable of binding DNA.

3. The method of claim 2 wherein said multivalent cations are selected from the group consisting of Fe(III), Cr(III), colloidal metal contaminants, and combinations thereof.

4. The method of claim 3 wherein said multivalent cations comprise Fe(III).

5. The method of claim 1 wherein said multivalent cations are selected from the group consisting of Fe(III), Cr(III), colloidal metal contaminants, and combinations thereof.

6. The method of claim 5 wherein said multivalent cations comprise Fe(III).

7. The method of claim 5 wherein said multivalent cations comprise Cr(III).

8. The method of claim 1 wherein said polynucleotide fragments are separated based on the size of said polynucleotide fragments.

9. The method of claim 1 wherein said polynucleotide fragments are separated based on the polarity of said polyucleotide fragments.

10. The method of claim 1, wherein said surfaces are comprised of material selected from the group consisting of titanium, coated stainless steel, sapphire, ceramic, and organic polymer.

11. The method of claim 10 wherein said surfaces comprise PEEK.

12. The method of claim 1, wherein said surfaces have been subjected to a multivalent cation removal treatment.

13. The method of claim 12 wherein said treatment comprises contacting said surfaces with an aqueous solution containing a member selected from the group consisting of nitric acid, phosphoric acid, pyrophosphoric acid, chelating agent, and combinations thereof.

14. The method of claim 13 wherein said components comprise frits.

15. The method of claim 13 wherein said chelating agent comprises EDTA.

16. The method of claim 1 wherein said process solutions comprise mobile phase.

17. The method of claim 1, wherein said particles have been subjected to an acid wash treatment.

18. The method of claim 1 wherein said process solutions include mobile phase additive present in sufficient amount to capture said multivalent cation contaminants.

19. The method of claim 18 wherein said multivalent cation contaminants are selected from the group consisting of Fe(III), Cr(III), colloidal metal contaminants, and combinations thereof.

20. The method of claim 18 wherein said multivalent cation contaminants comprise Fe(III).

21. The method of claim 20 wherein said additive comprises chelating agent.

22. The method of claim 21 wherein said agent comprises EDTA.

23. The method of claim 22 wherein said polynucleotide fragments comprise RNA.

24. The method of claim 22 wherein said polynucleotide fragments comprise single-stranded DNA.

25. The method of claim 1 including degassing means for removing oxygen from said process solutions.

26. The method of claim 1 wherein said polynucleotide fragments comprise RNA.

27. The method of claim 1 wherein said polynucleotide fragments comprise single-stranded DNA.

28. The method of claim 1, wherein the polynucleotide fragments comprise double-stranded fragments.

29. The method of claim 1, wherein the polynucleotide fragments comprise single-stranded fragments.

30. The method of claim 1, wherein the polynucleotide fragments comprise 5 or more base pairs.

31. The method of claim 1, wherein said separation particles comprise alkylated non-porous polymer beads having an average diameter of about 1–100 microns.

32. The method of claim 1, wherein said particles comprise silica and wherein said process solutions comprise EDTA.

33. A method for separating a mixture of polynucleotide fragments during passage through a liquid chromatographic column containing a separation bed comprising Matched Ion Polynucleotide Chromatography particles, wherein the method comprises:

supplying and feeding process solutions entering the column with components having process solution-contacting surfaces which contact process solutions held therein or flowing therethrough, wherein said process solution-contacting surfaces are material which does not release multivalent cations into aqueous solutions held therein or flowing therethrough, whereby the column is protected from contamination of the contents thereof by multivalent cations capable of interfering with polynucleotide separation, wherein the polynucleotide fragments are separated by Matched Ion Polynucleotide Chromatography, and wherein said multivalent cations comprise Fe(III).

34. The method of claim 33, wherein said surfaces have been subjected to a multivalent cation removal treatment.

35. The method of claim 34 wherein the treatment comprises contacting said surfaces with an aqueous solution containing a member selected from the group consisting of nitric acid, phosphoric acid, pyrophosphoric acid, and chelating agents.

36. The method of claim 33 wherein said process solutions include a mobile phase additive present in sufficient amount to capture multivalent cation contaminants capable of interfering with polynucleotide separation.

37. The method of claim 36 wherein said additive comprises a chelating agent.

38. The method of claim 37 wherein said separation particles comprise silica.

39. The method of claim 38 wherein said agent comprises EDTA.

40. The method of claim 33, wherein the polynucleotide fragments comprise double-stranded fragments.

41. The method of claim 33, wherein the polynucleotide fragments comprise 5 or more base pairs.

42. The method of claim 33 wherein said polynucleotide fragments comprise RNA.

43. The method of claim 33 wherein said polynucleotide fragments comprise single-stranded DNA.

44. The method of claim 33 wherein said surfaces are comprised of material selected from the group consisting of titanium, coated stainless steel, sapphire, ceramic, and organic polymer.

45. A method for separating a mixture of polynucleotide fragments during passage through a liquid chromatographic column containing a separation bed comprising Matched Ion Polynucleotide Chromatography separation particles, wherein the method comprises:

supplying and feeding process solutions entering the column with components having process solution-contacting surfaces which contact process solutions held therein or flowing therethrough, wherein said process solution-contacting surfaces are material which does not release multivalent cations into aqueous solutions held therein or flowing therethrough, whereby the column is protected from multivalent cation contamination of the contents thereof, wherein the polynucleotide fragments are separated by Matched Ion Polynucleotide Chromatography, and wherein said multivalent cations are selected from the group consisting of Fe(III), Cr(III), colloidal metal contaminants, and combinations thereof.

46. The method of claim 45 wherein said process solutions include a mobile phase additive present in sufficient amount to capture essentially any of said multivalent cations, and wherein said additive comprises a chelating agent.

47. The method of claim 46 wherein said chelating agent comprises EDTA.

48. The method of claim 47 wherein said separation particles comprise silica.

49. The method of claim 46 wherein said multivalent cations comprise contaminants capable of interfering with polynucleotide separation.

50. A method for separating a mixture of RNA fragments during passage through a liquid chromatographic column containing a separation bed comprising reverse phase separation particles, wherein the method comprises:
supplying and feeding process solutions entering the column with components having process solution-contacting surfaces which contact process solutions held therein or flowing therethrough,
wherein said process solution-contacting surfaces are material which does not release multivalent cations into aqueous solutions held therein or flowing therethrough,
whereby the column is protected from contamination of the contents thereof by multivalent cations selected from the group consisting of Fe(III), Cr(III), colloidal metal contaminants and combinations thereof,
wherein said particles comprise silica,
wherein said particles are substantially free from multivalent cations selected from the group consisting of Fe(III), Cr(III), colloidal metal contaminants, and combinations thereof,
wherein the RNA fragments are separated by reverse phase ion pair chromatography,
and wherein said process solutions comprise EDTA.

51. The method of claim 50 wherein said components comprise titanium or PEEK frits.

52. A method for separating a mixture of single-stranded DNA fragments during passage through a liquid chromatographic column containing a separation bed comprising reverse phase separation particles, wherein the method comprises:
supplying and feeding process solutions entering the column with components having process solution-contacting surfaces which contact process solutions held therein or flowing therethrough,
wherein said process solution-contacting surfaces are material which does not release multivalent cations into aqueous solutions held therein or flowing therethrough,
whereby the column is protected from contamination of the contents thereof by multivalent cations selected from the group consisting of Fe(III), Cr(III), colloidal metal contaminants, and combinations thereof,
wherein said particles comprise silica,
wherein said particles are substantially free from multivalent cations selected from the group consisting of Fe(III), Cr(III), colloidal metal contaminants, and combinations thereof,
wherein the single-stranded DNA fragments are separated by reverse phase ion pair chromatography,
and wherein said process solutions comprise EDTA.

53. The method of claim 52 wherein said components comprise titanium or PEEK frits.

54. A method for separating a mixture of double-stranded DNA fragments during passage through a liquid chromatographic column containing a separation bed comprising reverse phase separation particles, wherein the method comprises:
supplying and feeding process solutions entering the column with components having process solution-contacting surfaces which contact process solutions held therein or flowing therethrough,
wherein said process solution-contacting surfaces are material which does not release multivalent cations into aqueous solutions held therein or flowing therethrough,
whereby the column is protected from contamination of the contents thereof by multivalent cations selected from the group consisting of Fe(III), Cr(III), colloidal metal contaminants, and combinations thereof,
wherein said particles comprise silica,
wherein said particles are substantially free from multivalent cations selected from the group consisting of Fe(III), Cr(III), colloidal metal contaminants, and combinations thereof,
wherein the double-stranded DNA fragments are separated by reverse phase ion pair chromatography,
and wherein said process solutions comprise EDTA.

55. The method of claim 54 wherein said components comprise titanium or PEEK frits.

* * * * *